United States Patent
Mosler et al.

(10) Patent No.: US 11,058,860 B2
(45) Date of Patent: *Jul. 13, 2021

(54) TRANSFER DEVICE VALVE

(71) Applicant: Poly Medicure Limited, Faridabad (IN)

(72) Inventors: Theodore J. Mosler, Durham, NC (US); Edward P. Browka, Durham, NC (US)

(73) Assignee: POLY MEDICURE LIMITED, New Delhi (IN)

( * ) Notice: Subject to any disclaimer, the term of this patent is extended or adjusted under 35 U.S.C. 154(b) by 23 days.

This patent is subject to a terminal disclaimer.

(21) Appl. No.: 16/373,422

(22) Filed: Apr. 2, 2019

(65) Prior Publication Data

US 2019/0224469 A1 Jul. 25, 2019

Related U.S. Application Data

(63) Continuation of application No. 14/777,162, filed as application No. PCT/US2014/030897 on Mar. 17, 2014, now Pat. No. 10,286,202.

(Continued)

(51) Int. Cl.
*A61M 39/22* (2006.01)
*A61M 39/24* (2006.01)
(Continued)

(52) U.S. Cl.
CPC .......... *A61M 39/225* (2013.01); *A61M 39/24* (2013.01); *A61J 1/2044* (2015.05);
(Continued)

(58) Field of Classification Search
CPC ................ A61M 39/225; A61M 39/24; A61M 2039/1033; A61M 2039/242;
(Continued)

(56) References Cited

U.S. PATENT DOCUMENTS 3,993,066 A 11/1976 Virag
4,332,249 A * 6/1982 Joslin .................. A61M 5/3145
604/36

(Continued)

FOREIGN PATENT DOCUMENTS

EP 474069 A1 3/1992
WO 9000071 A1 1/1990
(Continued)

OTHER PUBLICATIONS

Infield Medical, LLC; International Search Report and Written Opinion for International Application No. PCT/US2014/030897 dated Aug. 27, 2014, 16 Pages.

(Continued)

*Primary Examiner* — Nathan R Price
*Assistant Examiner* — Courtney B Fredrickson
(74) *Attorney, Agent, or Firm* — Christopher J. Knors; Moore & Van Allen PLLC

(57) ABSTRACT

A valve is disclosed, the valve comprising a housing having an first opening and a second opening, and an elastomeric member positioned in the housing, the elastomeric member comprising a thickness, a continuous peripheral wall projecting from the thickness, and a slit extending through the thickness, a continuous portion of the peripheral wall creating a continuous sealable contact with the housing and partitioning the housing into an upper section and a lower section, the elastomeric member configured such that upon creating a pressure differential between the upper section and the lower section of the housing causes either: (i) the peripheral wall to deflect from the housing permitting fluid flow around the elastomeric member; or (ii) the slit to open permitting fluid flow through the elastomeric member. Methods using the valve are also disclosed.

25 Claims, 16 Drawing Sheets

Related U.S. Application Data

(60) Provisional application No. 61/852,286, filed on Mar. 16, 2013.

(51) Int. Cl.
*A61J 1/20* (2006.01)
*A61M 39/10* (2006.01)

(52) U.S. Cl.
CPC ............... *A61M 2039/1033* (2013.01); *A61M 2039/242* (2013.01); *A61M 2039/2426* (2013.01); *A61M 2039/2446* (2013.01); *A61M 2039/2466* (2013.01)

(58) Field of Classification Search
CPC .. A61M 2039/2426; A61M 2039/2446; A61M 2039/2466
See application file for complete search history.

(56) References Cited

U.S. PATENT DOCUMENTS

| | | | |
|---|---|---|---|
| 4,749,003 A | 6/1988 | Leason | |
| 4,871,356 A | 10/1989 | Haindl et al. | |
| 4,919,167 A | 4/1990 | Manska | |
| 5,112,301 A | 5/1992 | Fenton et al. | |
| 5,156,600 A | 10/1992 | Young | |
| 5,405,323 A | 4/1995 | Rogers et al. | |
| 5,453,097 A | 9/1995 | Paradis | |
| 5,465,938 A | 11/1995 | Werge et al. | |
| 5,660,205 A | 8/1997 | Epstein | |
| 5,984,902 A | 11/1999 | Moorehead | |
| 6,409,707 B1 | 6/2002 | Guala | |
| 7,291,133 B1 | 11/2007 | Kindler et al. | |
| 7,641,174 B2 | 1/2010 | Enerson et al. | |
| 7,673,653 B2 | 3/2010 | Mijers et al. | |
| 7,931,627 B2 | 4/2011 | Fangrow, Jr. | |
| 7,951,121 B2 | 5/2011 | Weaver et al. | |
| 8,034,035 B2 | 10/2011 | Weaver et al. | |
| 8,057,442 B2 | 11/2011 | Dikeman et al. | |
| 8,162,006 B2 | 4/2012 | Guala | |
| 8,187,234 B2 | 5/2012 | Weaver et al. | |
| 8,211,089 B2 | 7/2012 | Winsor et al. | |
| 8,257,320 B2 | 9/2012 | Feith et al. | |
| 8,276,616 B2 | 10/2012 | Wright et al. | |
| 8,758,305 B2 | 6/2014 | McMahon | |
| 2003/0029503 A1 | 2/2003 | Williamson et al. | |
| 2004/0186444 A1 | 9/2004 | Daly et al. | |
| 2005/0171490 A1 | 8/2005 | Weaver et al. | |
| 2005/0256460 A1 | 11/2005 | Rome et al. | |
| 2006/0142700 A1 | 6/2006 | Sobelman et al. | |
| 2007/0142729 A1 | 6/2007 | Pfeiffer et al. | |
| 2007/0161940 A1 | 7/2007 | Blanchard et al. | |
| 2008/0215014 A1 | 9/2008 | Nordgren | |
| 2009/0177187 A1 | 7/2009 | Weaver Quigley et al. | |
| 2009/0264832 A1 | 10/2009 | Dikeman et al. | |
| 2010/0030164 A1 | 2/2010 | Kimball et al. | |
| 2010/0152680 A1 | 6/2010 | Mcmahon | |
| 2010/0191192 A1 | 7/2010 | Prasad et al. | |
| 2012/0059312 A1 | 3/2012 | Dikeman et al. | |
| 2012/0130319 A1 | 5/2012 | Moorehead et al. | |
| 2012/0220955 A1 | 8/2012 | Maseda et al. | |
| 2012/0271247 A1 | 10/2012 | Weaver et al. | |
| 2013/0090608 A1 | 4/2013 | Stout et al. | |
| 2013/0160866 A1 | 6/2013 | Zinn et al. | |

FOREIGN PATENT DOCUMENTS

| | | |
|---|---|---|
| WO | 2004082757 A1 | 9/2004 |
| WO | 2005011799 A1 | 2/2005 |
| WO | 2014153302 A1 | 9/2014 |

OTHER PUBLICATIONS

International Bureau of WIPO; International Preliminary Report on Patentability for International Application No. PCT/US2014/030897 dated Oct. 1, 2015, 11 Pages.
USPTO; Final Office Action for U.S. Appl. No. 16/169,898 dated Nov. 26, 2019, 8 Pages.
USPTO; Notice of Allowance for U.S. Appl. No. 16/169,898 dated Dec. 11, 2019, 9 Pages.
USPTO; Corrected Notice of Allowability for U.S. Appl. No. 16/169,898 dated Feb. 26, 2020, 13 Pages.

\* cited by examiner

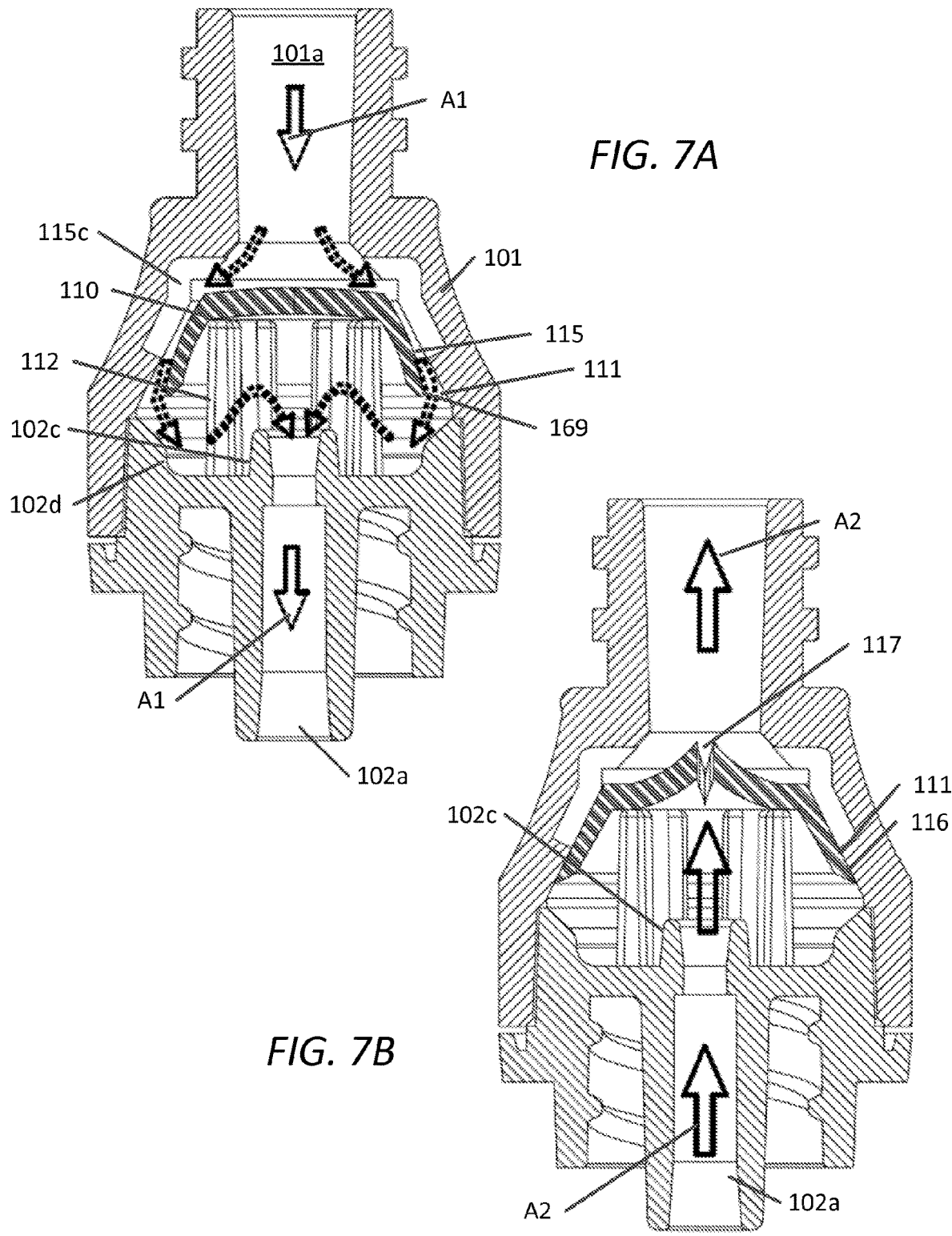

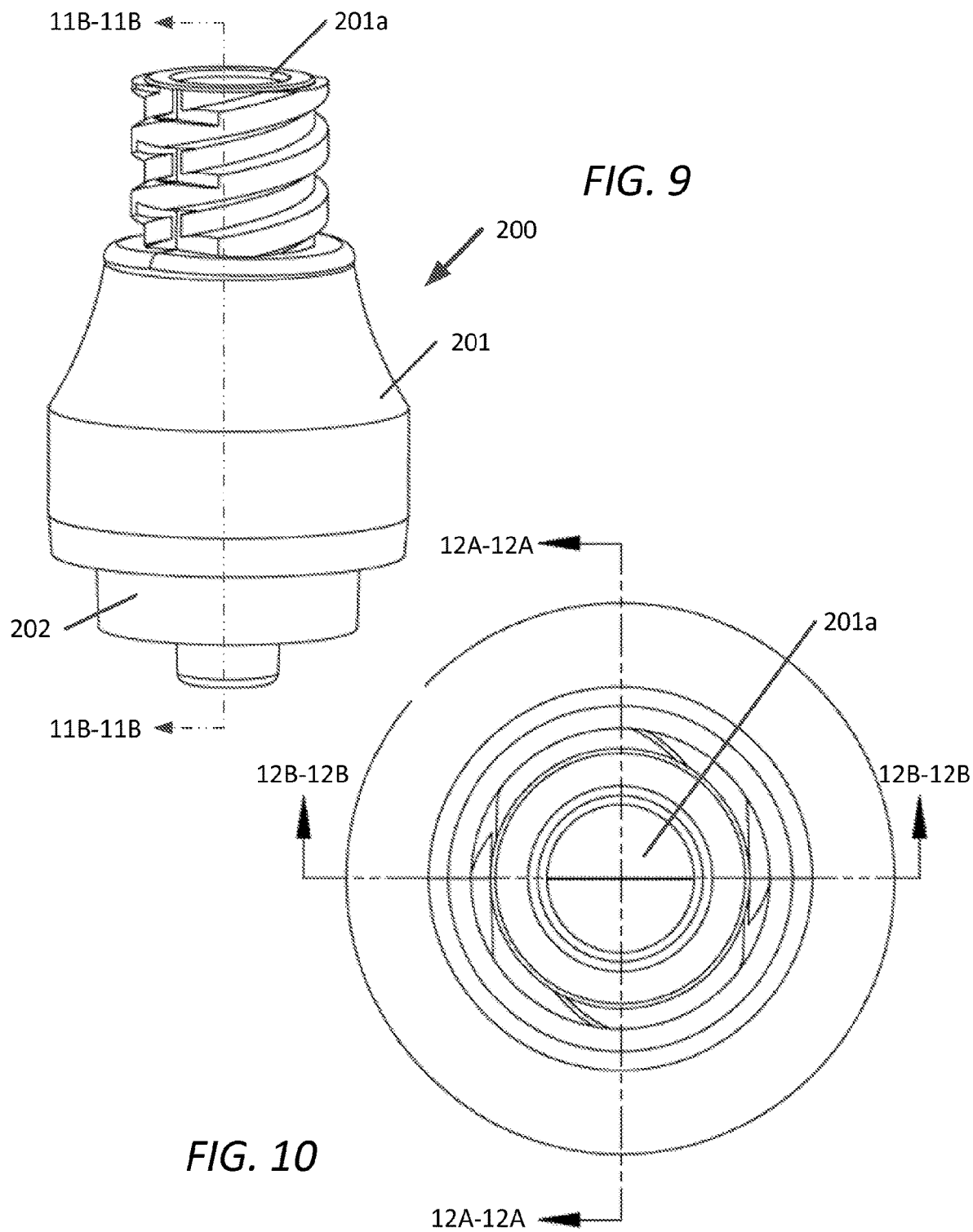

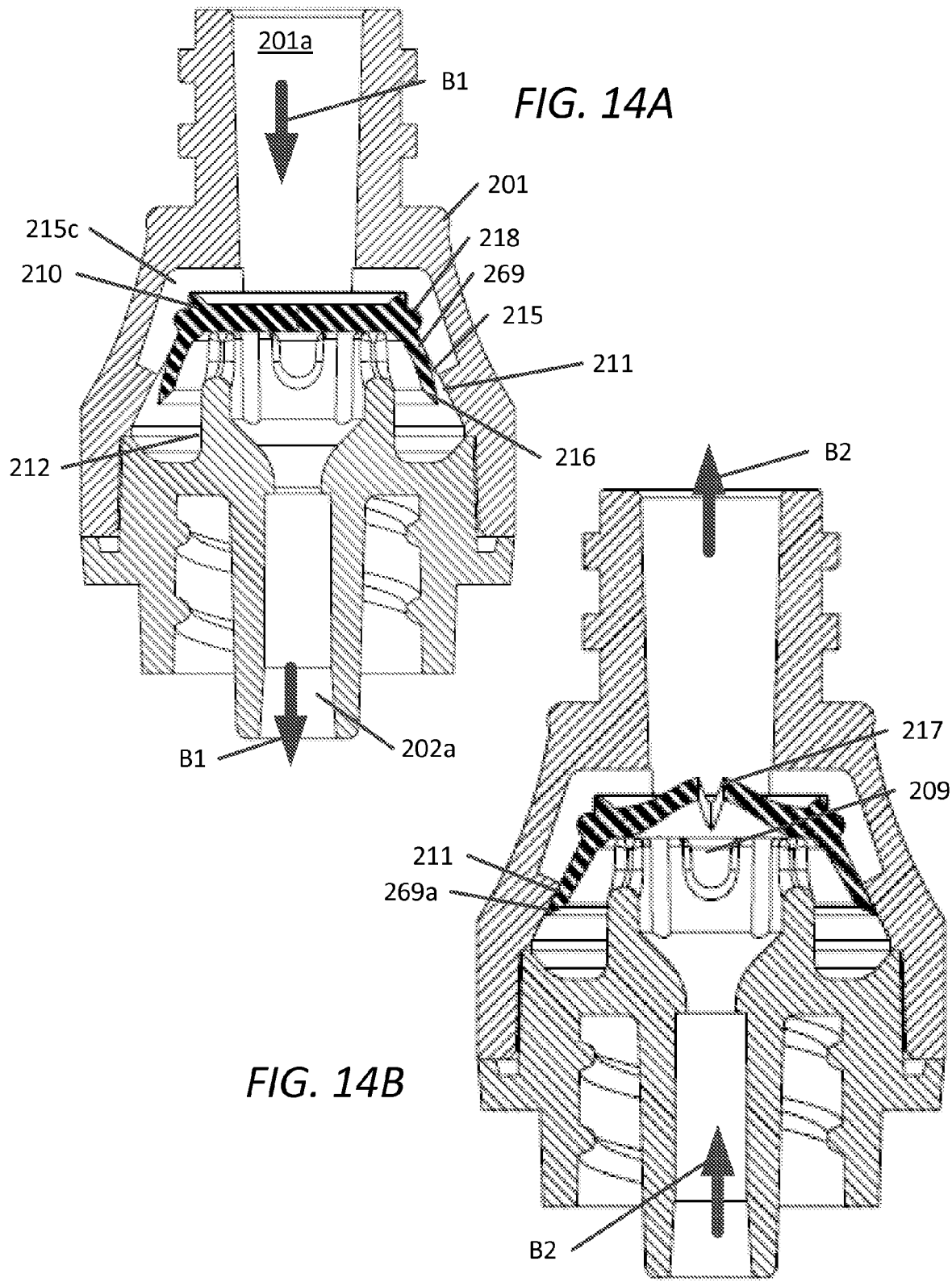

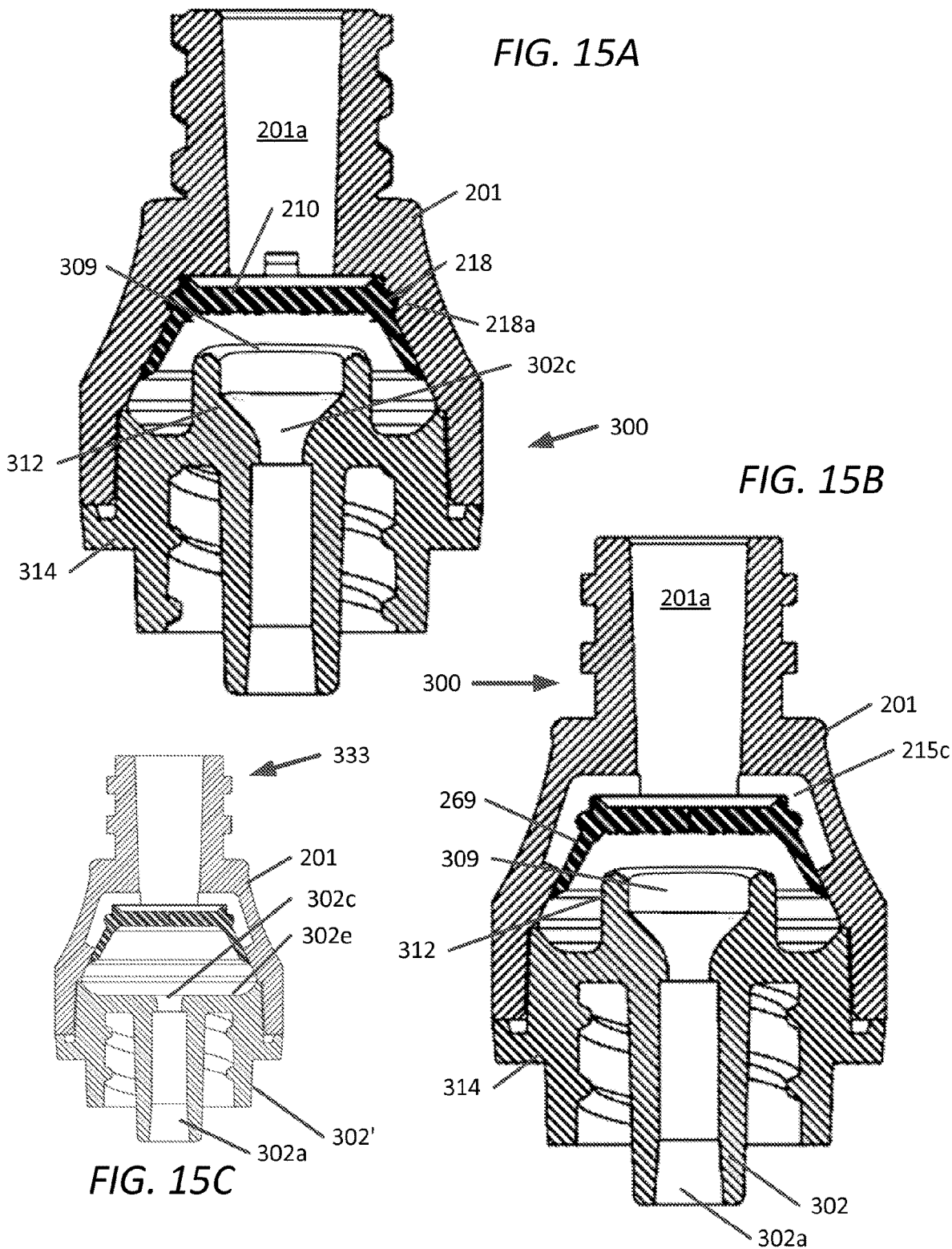

TRANSFER DEVICE VALVE

CROSS-REFERENCE TO RELATED APPLICATIONS

This application is a continuation application of U.S. patent application Ser. No. 14/777,162, filed Sep. 15, 2015, which was filed under the provisions of 35 U.S.C. § 371 and claims the benefit of International Patent Application No. PCT/US2014/030897, filed on Mar. 17, 2014, which claims the benefit of U.S. Provisional Application No. 61/852,286, filed on Mar. 16, 2013, the contents of which are incorporated herein by reference in their entirety.

TECHNICAL FIELD

The present disclosure relates generally to transfer devices for use with medicinal substances. More particularly, the disclosure concerns a pressure controlled valve device.

BACKGROUND

Blood reflux into central line and other types of vascular catheters can lead to intraluminal thrombosis, creating a full or partial occlusion of the IV access device. Such occlusions can interfere with IV therapy, provide a nutrient-rich area for pathogenic bacteria, or be detached from the catheter, leading to venous thrombosis. Even in cases where intraluminal thrombosis does not lead to further health complications, such a condition requires the replacement of the catheter, a procedure which can be both time consuming and lead to injury at the removal site and the new introduction site.

SUMMARY

In a first embodiment, a valve is provided. The valve comprises a housing having an first opening and a second opening; and an elastomeric member positioned in the housing, the elastomeric member comprising a thickness, a continuous peripheral wall projecting from the thickness; and a slit extending through the thickness, a continuous portion of the peripheral wall creating a continuous sealable contact with the housing and partitioning the housing into an upper section and a lower section, the elastomeric member configured such that upon creating a pressure differential between the upper section and the lower section of the housing causes either: (i) the peripheral wall to deflect from the housing permitting fluid flow around the elastomeric member; or (ii) the slit to open permitting fluid flow through the elastomeric member.

In an aspect of the first embodiment, the valve further comprises a support positioned in the housing and surrounded by the peripheral wall, the support configured to provide fluid communication between the first opening and the second opening. In another aspect, alone or in combination with any of the previous aspects of the first embodiment, the support member is received by or integral with the housing. In another aspect, alone or in combination with any of the previous aspects of the first embodiment, the support member comprises a plurality of spaced apart columns arranged about the second opening, the distal ends of the plurality of columns surrounded by the peripheral wall. In another aspect, alone or in combination with any of the previous aspects of the first embodiment, the support member comprises an annular wall arranged around the second opening, the annular wall having at least one fluid flow passage providing fluid communication between the lower section and the second opening.

In another aspect, alone or in combination with any of the previous aspects of the first embodiment, the second opening comprises a conduit that extends into the housing and is surrounded the peripheral wall. In another aspect, alone or in combination with any of the previous aspects of the first embodiment, a portion of the conduit extending into the housing is of a larger internal diameter than the conduit extending external to the housing.

In another aspect, alone or in combination with any of the previous aspects of the first embodiment, a portion of housing is tapered and a distal portion of the peripheral wall tapers in sealable contact therewith.

In another aspect, alone or in combination with any of the previous aspects of the first embodiment, the upper portion of the housing comprises an interior wall, the interior wall comprising at least one recessed channel therein and extending substantially along the longitudinal axis of the housing, wherein deflection of the peripheral wall from the housing substantially corresponds to the placement of the at least one recessed channel.

In another aspect, alone or in combination with any of the previous aspects of the first embodiment, the housing comprises two or more components sealably connectable to form a fluid tight assembly.

In another aspect, alone or in combination with any of the previous aspects of the first embodiment, the thickness comprises a top surface and a bottom surface separated from the top surface by the thickness; and the peripheral wall has a second thickness, and the peripheral wall projects from the bottom surface. In another aspect, alone or in combination with any of the previous aspects of the first embodiment, the second thickness is less than the thickness between the top and bottom surfaces.

In another aspect, alone or in combination with any of the previous aspects of the first embodiment, the elastomeric member further comprises a continuous lateral protrusion along the peripheral edge of the thickness, and the housing is configured with a corresponding recess to receive the continuous lateral protrusion and to provide a radial stress to the surface of the elastomeric member. In another aspect, alone or in combination with any of the previous aspects of the first embodiment, the elastomeric member further comprises one or more vertical protrusions on the top surface, the housing being configured to provide a normal stress to the one or more vertical protrusions.

In other aspect, alone or in combination with any of the previous aspects of the first embodiment, the thickness is concave, convex, or concave and convex on opposing sides of the thickness.

In another aspect, alone or in combination with any of the previous aspects of the first embodiment, the elastomeric member is annular, oval, cylindrical, hemispherical, or cup-shaped. In another aspect, alone or in combination with any of the previous aspects of the first embodiment, the elastomeric member is conical frustum-shaped.

In another aspect, alone or in combination with any of the previous aspects of the first embodiment, the top surface of the elastomeric member has one or more fluid channels terminating at the peripheral edge.

In another aspect, alone or in combination with any of the previous aspects of the first embodiment, the slit opens at a threshold pressure greater than a threshold pressure required to deflect the peripheral wall from the housing.

In another aspect, alone or in combination with any of the previous aspects of the first embodiment, the slit, in combination with the first opening and the second opening, is configured to receive an elongated medical device through the housing. In another aspect, alone or in combination with any of the previous aspects of the first embodiment, the support is configured to receive and/or guide an elongated medical device through the housing. In another aspect, alone or in combination with any of the previous aspects of the first embodiment, the support in combination with the slit is configured to receive and/or guide an elongated medical device through the housing.

In a second embodiment, a method of controlling flow direction through a device is provided. The method comprising: creating, in a device comprising the valve as defined in any of aspects of the first embodiment, a pressure differential between the upper section and the lower section of the housing; causing the peripheral wall to deflect from the housing and permitting fluid flow around the elastomeric member; or, in the alternative; causing the slit to open permitting fluid aspiration through the elastomeric member; wherein fluid flow direction through the device is controlled.

In a first aspect, alone or in combination with any of the previous aspects of the second embodiment, the pressure differential between the upper section and the lower section of the housing is created by a negative pressure applied to the upper section of the housing or by a positive pressure applied to the lower section of the housing so that the slit permits fluid flow therethrough.

In another aspect, alone or in combination with any of the previous aspects of the second embodiment, the pressure differential between the upper section and the lower section of the housing is created by a positive pressure applied to the upper section of the housing so that the peripheral wall permits fluid flow around the elastomeric member.

In another aspect, alone or in combination with any of the previous aspects of the second embodiment, the method further comprises introducing a flushing solution to the upper portion of the housing via the first opening; causing, by positive pressure, deflection of the peripheral wall from the housing; urging the flushing solution around the elastomeric member; re-directing fluid flow in the lower section of the housing; and cleaning at least a portion of the lower section of the housing.

In another aspect, alone or in combination with any of the previous aspects of the second embodiment, the cleaning further comprises preventing thrombus within the device after aspiration of biological fluid through the device or preventing bacterial growth within the device after aspiration. In another aspect, alone or in combination with any of the previous aspects of the second embodiment, the method further comprises preventing reflux within the device.

BRIEF DESCRIPTION OF THE DRAWINGS

FIG. 7A and FIG. 7B are cross-sectional views of the embodiment of FIG. 1 along sectional planes 4A-4A and 4B-4B, respectively, in a first state of operation and in a second state of operation, respectively;

FIG. 9 is a plan view, with sectional planes B-B, of another embodiment of a pressure activated valve in accordance with the present disclosure;

FIG. 10 is a top view of FIG. 1 showing sectional planes 12A-12A and 12A-12A;

FIG. 14A and FIG. 14B are cross-sectional views of the embodiment of FIG. 9 along sectional planes 12A-2A and 12B-12B, respectively, in a first state of operation and in a second state of operation, respectively;

FIGS. 15A, 15B, and 15C are sectional views of another embodiment of a pressure activated valve in accordance with the present disclosure, FIG. 15B showing the embodiment of FIG. 15A rotated 90°;

DETAILED DESCRIPTION

Figure 1:
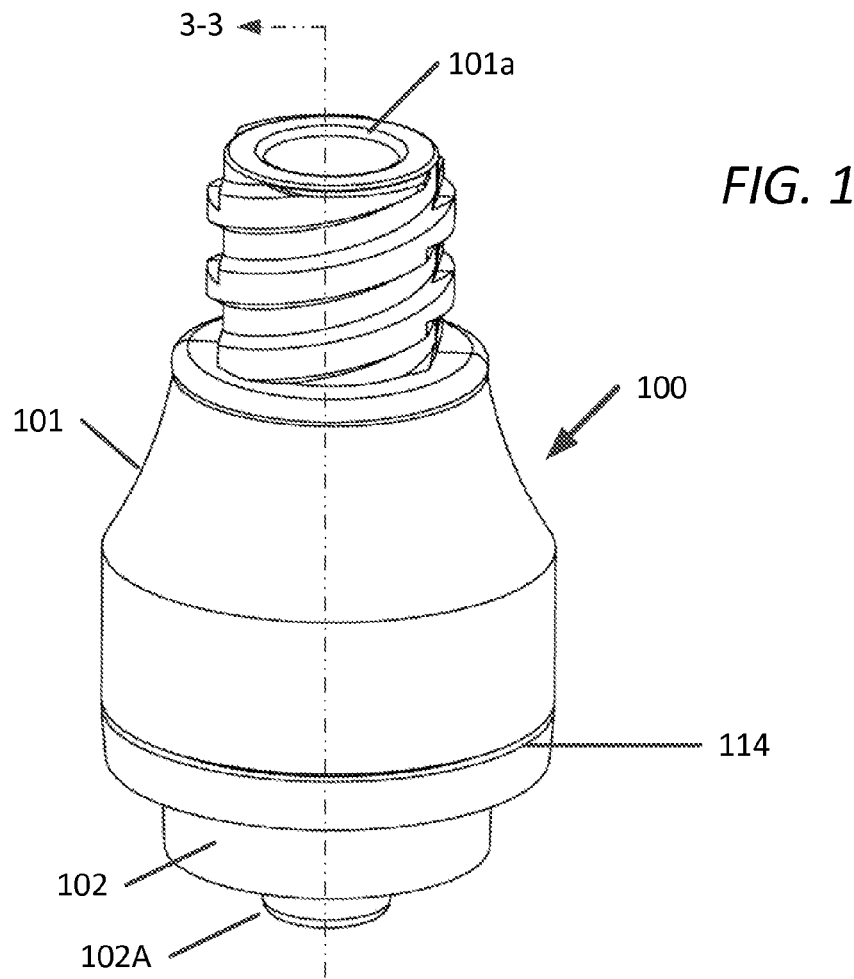
FIG. 1 is a plan view, with sectional plane A-A, of an embodiment of a pressure activated valve in accordance with the present disclosure.

The valve of the present disclosure, and devices comprising the valve, reduce or eliminate reflux of blood into the distal tip of a vascular catheter. Devices comprising the valve of the present disclosure can be used as a stand-alone replacement for an open Luer or used in conjunction with an existing IV access valve, even when use of the IV access valve alone would create blood reflux from a negative bolus. The valve has, by design, a high injection direction flow rate and a high internal fluid mixing, preventing un-flushable fluid volumes which could lead to bacterial colonization and catheter related blood stream infection (CRBSI). These two primary benefits are not readily available in the valves and devices present in the art.

The presently disclosed valve which can also be referred to as a "pressure activated valve," or, alternatively referred to as an "infusion patency valve," is a valve suitable for assembly in a device, such as a medical device. The valve comprises an elastomeric member configured to reside in a housing, the elastomeric member having a slit through a thickness, the elastomeric member further having a deflectable peripheral wall in interference contact with the housing interior so as to form a fluid-tight seal and to partition the housing into an upper and lower portion. Each partition having associated therewith an opening for fluid egress and ingress.

In one aspect, the disclosed valve allows for a low-head pressure delivery of fluids in one-direction to flow through the valve and openings of a device. This type of fluid delivery is consistent with both continuous IV therapy and periodic delivery by injection or IV pump. When fluid, either through an attached Luer or other infusion device, is introduced into the proximal end of a device comprising the disclosed patency valve, a pressure differential is created between partitions in the housing. The pressure differential, in one state, deflects the peripheral wall surface of the elastomeric member, breaking a fluid-tight seal with the housing. This permits the flow of fluid around the elastomeric member and through this temporary junction, and introduces fluid into the other partition of the housing separated by the elastomeric member.

In one state, e.g., infusion, where there is a positive pressure differential formed between the upper and the lower partitions of the housing, the valve of the present disclosure provides a low valve cracking pressure. In addition to the low cracking pressure, the valve of the present disclosure further provides a low restriction to flow in the infusion direction (proximal to distal flow direction) which allows devices comprising the valve to be used with existing IV infusion systems. The low, but non-zero, cracking pressure of the valve described herein still prevents the ingress of air in the infusion direction when the valve is near the vertical level of the injection site. This is provided, among other things, by arranging flowing around the elastomeric member, and configuring the internal design of the housing so as to aid in valve flushability while providing for a high flow rate.

In another state, e.g., aspiration, where there is a negative pressure differential formed between the upper and the lower partitions of the housing, the valve of the present disclosure provides a higher threshold cracking pressure than in the infusion direction. This configuration of the presently disclosed valve, among other things, prevents reflux of blood into the catheter lumen, typically resulting from a transient vacuum caused by the disconnection of a Luer, infusion accessory, or needle-free access valve. As a result of the design and configuration of the presently disclosed valve and devices comprising same, the prevention of blood reflux is provided and the risk of intraluminal thrombosis, and bacterial colonization or infection is therefore, reduced or eliminated. The cracking pressure of the presently disclosed valve in the aspiration direction is configured such that it is still low enough to permit the deliberate withdrawal of fluids using a syringe or vacuum tube, as is conventionally performed.

Another advantage of the presently disclosed valve or devices comprising same is the configuration of the valve within the device provides for high fluid mixing and/or flushing of blood-contacted surfaces. The fluid volume and/or velocity in the infusion direction is controlled so as to maximize fluid mixing in the partitioned space of the device. This high degree of mixing improves flushing of the valve, limiting dead volume that could otherwise lead to bacterial colonization from un-flushed nutrient-rich infusates.

The presently disclosed valve is configured in one embodiment to be attached to one end of a medical device having a lumen, such as a catheter, and is designed, among other things, to prevent the reflux of blood or other fluids into the lumen or lumens of the medical device adapted to the patency valve connector. Inclusion of the valve, either alone or in a connector, can be used in combination with or integral with a medical device having a lumen, e.g., a vascular catheter, and can be configured for coupling with such devices or be configured for integration during the manufacture of the catheter, or later, at the point of use.

One advantage of the presently disclosed valve and devices comprising same is that detachment of an accessing Luer-attached device from a proximal end of a device comprising the present valve, or detachment from a needle-free access valve attached to the proximal end of a device comprising the present valve will not cause the reflux of blood into the central line lumen(s). Moreover, a device comprising the present valve will still permit the withdrawal of fluids, such as blood or other biological fluids, through the lumen by an accessing syringe or vacuum vial (Vacutainer, e.g.).

In one aspect, the valve comprises a housing and an elastomeric member. In another aspect, the valve comprises a housing, and elastomeric member, and a support. The various aspects of the valve are now discussed in reference to exemplary embodiments and/or the accompanying drawings.

The housing comprising the valve can comprises a single component or be of a multi-component configuration. In one aspect, the housing comprises an upper section and a lower section sealably connectable to the upper section to provide a watertight assembly. In another aspect, the housing comprises an upper section comprised of two or more parts that are sealably connectable to the lower section to provide a watertight assembly. The housing can be of a conventional plastic suitable for medical devices such as polycarbonate, polyester, cyclic olefinic copolymer, ABS, and the like.

The elastomeric member is configured to partition the housing into an upper and lower section. Generally, the elastomeric member can be annular, oval, cylindrical, hemispherical, cup-shaped or conical frustum-shaped. In one aspect, the elastomeric member can be cup-shaped or conical frustum-shaped with an internal cavity formed between its base and its surface. In one aspect, a horizontal or convex/concave surface with a peripheral wall projection from that surface forming a cup-shape or a conical frustum-shape can advantageously be used. The peripheral wall from such construction can be oval or round, or of another shape, provided a continuous fluid-tight seal can be cooperatively arranged with an interior portion of the housing and a portion of the outer surface of the peripheral wall so as to partition the housing into an upper and a lower portion, and provide flow direction functionality to the valve or the device. The peripheral wall can taper away from the surface it projects from or project normal thereto. Alternatively or in combination with a taper, the outer diameter of the peripheral wall and/or the surface it projects from can be greater than a corresponding inner diameter of the corresponding mating portion of the housing so as to provide the interference and/or fluidic seal and/or partitioning of the housing. The taper angle of the peripheral wall can be greater than the taper of the interior wall of the housing to provide an interference relationship of an amount capable of facilitating a fluid-tight seal there between and to effectively partition the housing of the device into at least two sections. Alternatively or in combination with the above, the peripheral wall thickness can be tapered toward its distal end.

In one aspect, the elastomeric member comprises a conical frustum shape having a surface, the surface having a top surface and a bottom surface separated from the top surface by a first thickness, and the peripheral wall projecting away from the bottom surface has a second thickness, the peripheral wall forming a cavity that includes the bottom surface. The second thickness can be less than or equal to the first thickness. The surfaces can be concave and convex on opposing sides or can be concave or convex on one side only. The top surface of the elastomeric member can have one or more fluid channels terminating at its peripheral edge. Other features are described below and in the drawings.

The elastomeric member comprises one or more slits through a thickness so as to open upon a pressure differential between the upper and lower sections of the housing, which can be created for example, by withdrawal of fluid from either distal ends of a device comprising the elastomeric member. The slit of the elastomeric member is configured to open at a threshold pressure greater than a threshold pressure required to deflect the peripheral wall from the housing. The housing is configured such that headspace above the elastomeric member and the inside surface of the upper housing provides sufficient clearance for the slit to open. In a first state, the slit is resistant to flow in the proximal to distal flow direction (e.g., infusion) in one aspect, which, among other things, limits the capacity of the slit to open in this flow direction. However, flow in another direction (e.g., aspiration) is permitted through the slit.

In one aspect, the elastomeric member has a generally flat or convex/concave top surface, having a conical frustum-shaped cavity that includes a bottom surface supported by one or more supports (e.g., protruding columns or a wall) that project aligned with the longitudinal axis of housing. The support(s) can be integral with the lower housing or can be placed in position during manufacturing. An interference fit of at least a portion of the elastomeric member is maintained by features on either the upper and/or or lower housings components and/or the elastomeric member. The elastomeric member may also be secured in place via an annular fitment or projection with or without said support(s) to position the elastomeric member during manufacturing and device use and/or provide a radial compressive stress to the slit (e.g., to adjust or control the slit cracking pressure). For example, the elastomeric member can comprises a continuous lateral protrusion along the peripheral edge of its top conical frustum surface, and the housing can be configured with a corresponding recess to receive the continuous lateral protrusion and to provide interference and/or a radial stress to the surface thickness of the elastomeric member. The continuous lateral protrusion can be of a thickness equal to or less than the thickness of the surface. In addition to or in combination with, the elastomeric member can comprise one or more vertical protrusions from its conical frustum top surface, the housing being configured and dimensioned to provide a normal stress to the one or more vertical protrusions for securing the elastomeric member during assembly or use.

In one aspect the elastomeric member is part of a valve assembly. The valve assembly can be configured for a variety of housing configurations designed for fluid coupling, such as two-way, three-way and four-way couplings. The valve assembly can comprise the elastomeric member and optional support configured for introduction into a housing. The assembly can be configured to adapt to a two-piece housing construct, either having a lower/upper housing, a two-piece housing separated along the longitudinal axis, or a combination thereof, e.g., a solid lower housing and a two-piece upper housing.

Withdraw of fluids through the infusion patency valve (fluid flow from in the distal to proximal direction) is restricted below the threshold cracking pressure of the slit(s) which are formed through the central axis of the elastomeric member. The threshold cracking pressure is designed to be high enough so that transient vacuum caused by the disconnection of a Luer, infusion accessory, or attached needle-free access valve, does not open the slit and hence, the valve to flow in that direction. However, the aspiration flow direction "cracking pressure" is designed to be low enough to permit the deliberate withdraw of fluid by syringe or vacuum tube, if needed. The design of the conical frustum-like section of the elastomeric member and its interference with the conical interior portion of the housing provides for one-way flow of fluid, operable in either direction, controlling the fluid flow in the housing between its openings with leak-free function and ease of use.

The valve and devices configured with this valve can be configured for passage of a medical device e.g., an introducer such as a guidewire or other medical device. Designs with the present valve can provide for an "over the guidewire" placement or replacement technique and eliminate or prevent bleed-back or air embolisms. In one aspect of the present disclosure each of the embodiments are exclusive of spring-actuated valve assemblies, or spring-actuated valve assemblies having an introducer valve within a cavity of the valve housing, or compression ring actuated valve assemblies. Of course, such devices can be used in combination with the presently disclosed valve. The valve embodiments disclosed herein eliminate the need for a triple layer design of a slit opening, followed by a hole, followed by another slit opening, for example. Indeed, in certain aspects, the present disclosure is devoid of pinching of the elastomeric member between halves of the housing for supporting the elastomeric member, whereas, instead, a design of the elastomeric member in cooperative relationship with the interior wall of the housing is employed. Likewise, the presently disclosed valve embodiments minimize dead space above and below the valve assembly and/or provides for effective flushing of any such dead space. Furthermore, the present valve embodiments avoid problems common to other configurations of pressure-actuated valves used in medical devices, such as: 1) leakage of fluids through "dome-like" septa having slits for two-way fluid transfer; 2) an inability to gravity feed through devices having a slit "trampolined" between walls of a housing; and 3) an inability to effectively flush the inside of the device with valves designed for two-fluid flow through the slit. The present valve, in contrast, provides for elimination of leakage, the ability to gravity feed, as well as improved flushing of the inside of the device comprising the valve. Moreover, additional advantages of the valve of the present disclosure includes the directional control of fluid flow through the device via passage either through or around the elastomeric member, the minimization of dead space and/or improved flushing capability, repeatable guidewire accessibility without failure or problems generally associated with known valved systems.

The elastomeric member can be fabricated from conventional thermoset rubbers (synthetic and non-synthetic). The elastomeric member is configured between the proximal and distal housings during manufacturing. The interference between the conical periphery of the elastomeric member and the conical portion of the proximal housing forms a normally closed valve. This interference, among other things, allows low pressure passage of liquids in one direction.

The design of the pressure activated/patency valve allows for the passage of a wire or cannula through the central axis of the device. This is helpful for placement of a PICC or CVC catheter, as well as a short peripheral IV catheter. Thus, the presently disclosed valve can serve to function as a "bloodless start" valve, thereby limiting exposure of blood to the clinician upon placement of the catheter. Upon insertion, the wire or needle cannula can be removed, the slit automatically closes upon its removal, and the caregiver is protected from excess exposure of blood. This may also keep the catheter hub more free of nutrient rich fluid to further protect the patient from possible infection of the site. The slit of the elastomeric member, in cooperation with the first opening and the second opening of the housing, can be configured to receive an elongated medical device through the housing. The housing may include a support or an inwardly tapered opening feeding into the second opening is configured to receive and/or guide an elongated medical device through the housing.

The above valve provides for a method of creating a pressure differential between the upper section and the lower section of a housing comprising the valve presently disclosed. This pressure differential causes either the peripheral wall to deflect from the housing and permitting fluid flow around the elastomeric member, or, in the alternative, causes the slit to open permitting fluid aspiration through the elastomeric member. In this method, fluid flow direction through the device is controlled. By way of example, the pressure differential between the upper section and the lower section of the housing is created by a negative pressure applied to the upper section of the housing or by a positive pressure applied to the lower section of the housing so that the slit permits fluid flow therethrough. In other example, the pressure differential between the upper section and the lower section of the housing is created by a positive pressure applied to the upper section of the housing so that the peripheral wall permits fluid flow around the elastomeric member.

The method further comprises introducing a flushing solution to the upper portion of the housing via the first opening and causing, by positive pressure, deflection of the peripheral wall from the housing. This results in the urging the flushing solution around the elastomeric member and under and in the cavity of the conical frustum-shaped elastomeric member, along with the re-directing of fluid flow in the lower section of the housing. This provides cleaning of at least a portion of the lower section of the housing. This cleaning prevents thrombus within the device after aspiration of biological fluid through the device and/or prevents bacterial growth within the device after aspiration.

The upper and lower housings of all embodiments herein disclosed may be secured by ultrasonic welding, solvent bonding, glue, adhesive, and/or other heat or chemical methods known in the art. In at least one aspect of the present disclosure, the housing or its subassemblies is designed such that the welding process will capture the elastomeric member between housings producing the normally-closed seal. Housings components can be configured for snap-fit, gluing, spin welding, solvent welding and the like.

Any part of elastomeric member and/or the slit of the elastomeric member may be lubricated. In one aspect, a silicone lubricant may be used. Different lubricants may be used on different surfaces of the elastomeric member. One or more silicone fluid may be compounded into the elastomeric member during molding.

The housing and/or supports can be injection-molded out of a rigid, biocompatible, engineering grade resin such as polycarbonate, cyclic olefinic copolymer (COC or transparent acrylonitrile butadiene styrene (MABS), and the like. Certain configurations of the elastomeric member may be constructed using a thermoplastic elastomer TPE, which is likewise injection molded. Liquid injection molding (LIM) can be used for the elastomeric member and/or to create the valve assembly. Compression molding or rotational compression molding can be used to manufacture the elastomeric member. Elastomeric materials can be of silicone, polyurethane for such molding methods.

Embodiments of the present disclosure now will be described more fully hereinafter with reference to the accompanying drawings, in which embodiments of the present disclosure are shown. This present disclosure may, however, be embodied in many different forms and should not be construed as limited to the embodiments set forth herein. Rather, these embodiments are provided so that this disclosure will be thorough and complete, and will fully convey the scope of the claims to those skilled in the art. Like numbers refer to like elements throughout.

Figure 2:
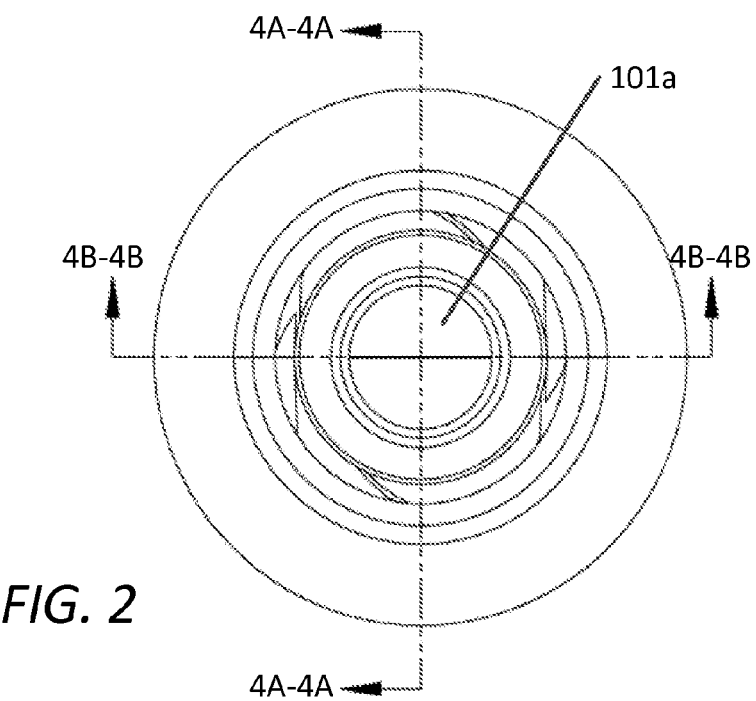
FIG. 2 is a top view of FIG. 1 showing sectional planes 4A-4A and 4B-4B.

Referring now to the Figures, FIG. 1 is a perspective view of a first embodiment depicting device 100. Device 100 comprises a rigid upper housing 101 for providing connection to a male Luer fitting, and a rigid lower housing 102, which provides for connection to a female Luer fitting. The device has a smooth exterior for patient comfort. Device 100 has a first opening 101a and a second opening 102a. While first opening 101a is shown as threaded, it can be configured smooth without threads. FIG. 2 is top view of device 100 showing sectional planes described further below.

Figure 3:
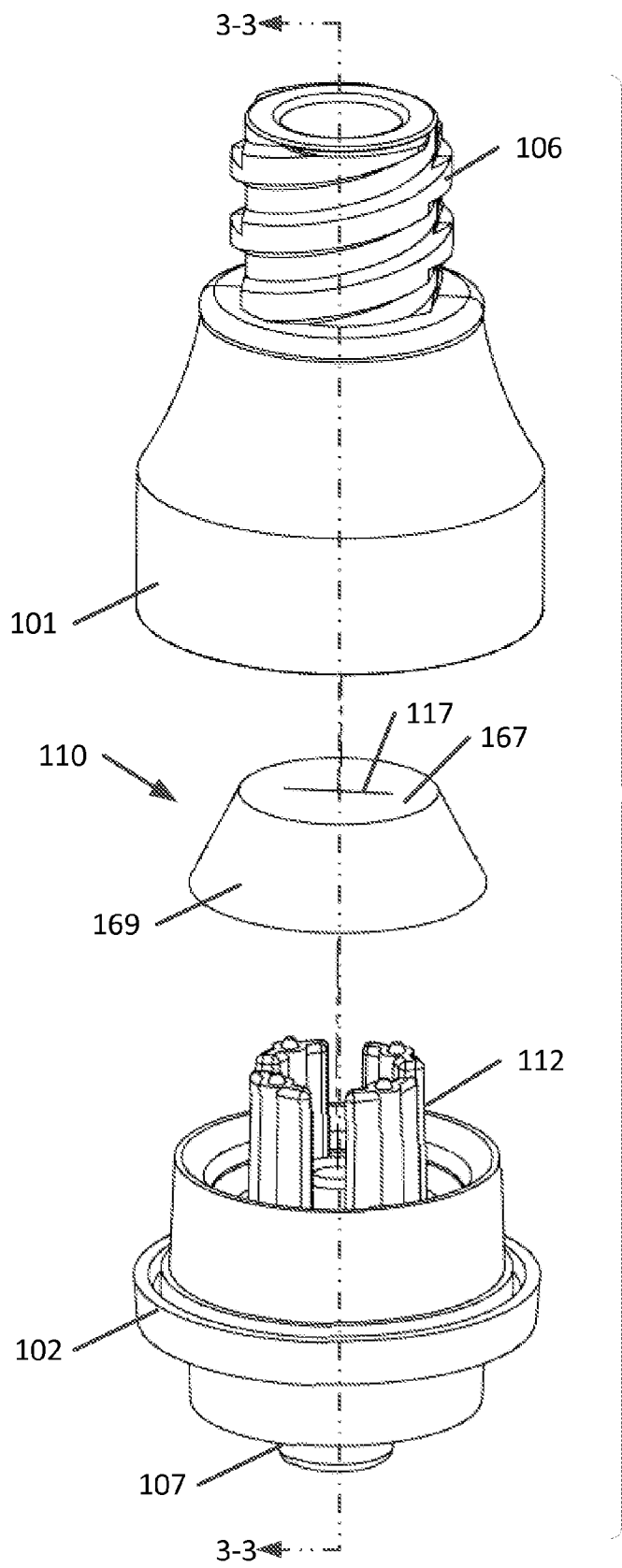
FIG. 3 is an exploded view of the embodiment of FIG. 1.

FIG. 3 is an exploded perspective view of device 100 depicting lower housing 102, having supports 112, elastomeric member 110 having peripheral wall 169 projecting from surface 167 towards lower housing 102. On surface 167 is slit 117. Upper housing 101 is configured to form fluid tight seal with lower housing 102. Upper housing 101 can be configured with threaded female Luer fittings 106, as shown. The lower housing can be configured with male luer 107 and surrounding internal threads 108, as shown.

Figure 4:
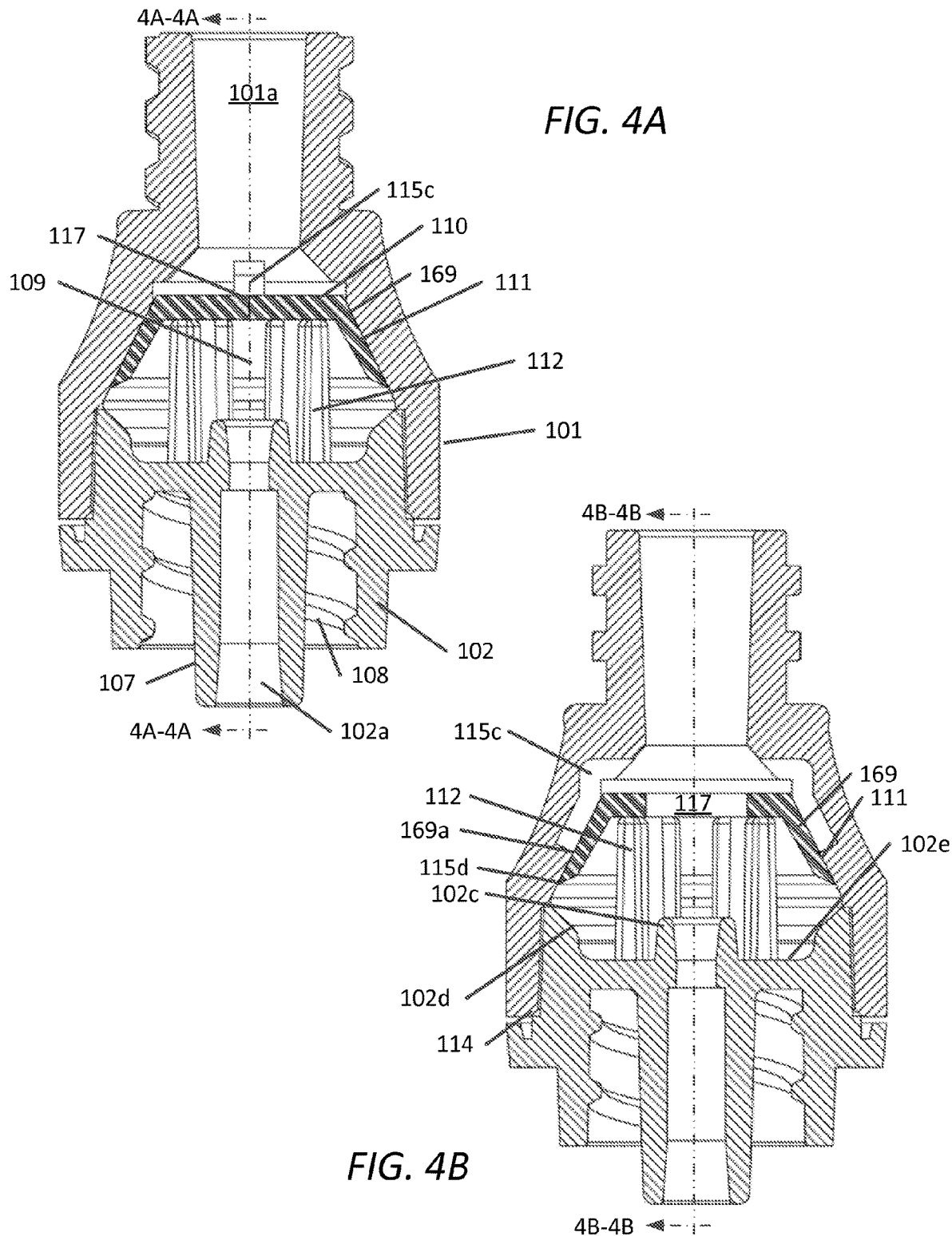
FIG. 4A and FIG. 4B are cross-sectional views of the embodiment of FIG. 1 along sectional planes 4A-4A and 4B-4B, respectively.

Referring now to FIGS. 4A and 4B, cross-sectional views, 90° apart respectively, of first embodiment device 100 in an assembled configuration are shown.

FIG. 4A depicts a portion of peripheral wall 169 of elastomeric member 110 having an interference fit with the interior wall 111 forming a continuous seal with the interior wall 111 of upper housing 101. Elastomeric member 110 partitions device 100 into an upper section corresponding to first opening 101a and lower section corresponding to second opening 102a. Elastomeric member 110 is shown supported by supports 112. Supports 112 form opening 109 and provide fluid communication between lower housing 102 and through second opening 102a. Elastomeric member 110 is shown here as a normally-closed valve, as both slit 117 and continuous seal with interior wall 111 prevent fluid flow between openings 101a and 102a prior to activation of device 100 via a pressure differential. The interference fit between elastomeric member 110 and interior wall 111 of the housing can be provided upon securing upper housing 101 and lower housing 102 during manufacturing e.g., upon bonding/welding the housings components together, for example at weld joint 114. The elastomeric member is supported by supports 112 and the elastomeric member is sealed against the interior wall 111 of the upper housing. Fluid is able to flow between the supports into opening 109 and through first opening 101a. Lower housing 102 includes base 102e surrounding projection 102c which projects from base 102e as part of second opening 102a. Surface (or base) 102e extends radially outward to tapered wall 102d. A portion of the outer diameter of tapered wall 102d is configured for sealable arrangement via weld joint 114 with an interior diameter of upper housing 101.

FIG. 4B depicts an aspect of the first embodiment whereby fluid channel 115c is provided in interior wall 111 of upper housing 101. As shown, fluid channel 115c extends generally parallel to the longitudinal axis of device 100 towards lower housing 102. The distal terminus of the length of fluid channel 115c (e.g., distal end 115d) is configured to be such that at least a portion of peripheral wall 169 (e.g., as shown, distal end 169a) remains continuously in interference with interior wall 111. In one embodiment, device 100 can be configured without fluid channel 115c (width equal 0).

In one aspect, two or more fluid channels 115c are provided in interior wall 111 of upper housing 101. In such an aspect, two fluid channels 115c can be arranged in a parallel configuration with both their corresponding longitudinal axes substantially aligned with the longitudinal axis of device 100. In one embodiment, elastomeric member has slit 117 formed of a single slit, and the two fluid channels 115c are arranged to be orthogonal with the longitudinal axis of the single slit 117. In this configuration, during infusion of fluid, and upon deflection of peripheral wall 169, radial forces are applied to surface 167 to facilitate maintaining closure of slit 117.

Figure 5:
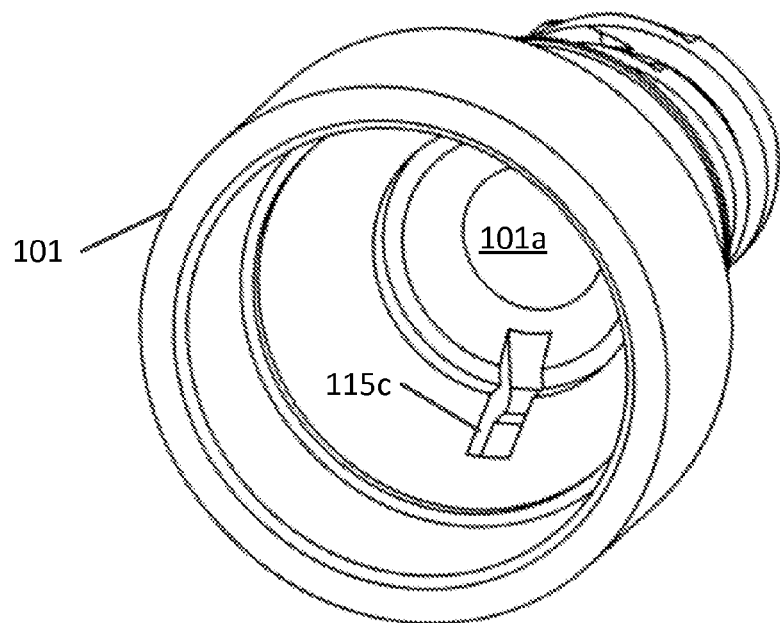
FIG. 5 is a perspective view of the upper housing of the embodiment of FIG. 1.
Figure 6:
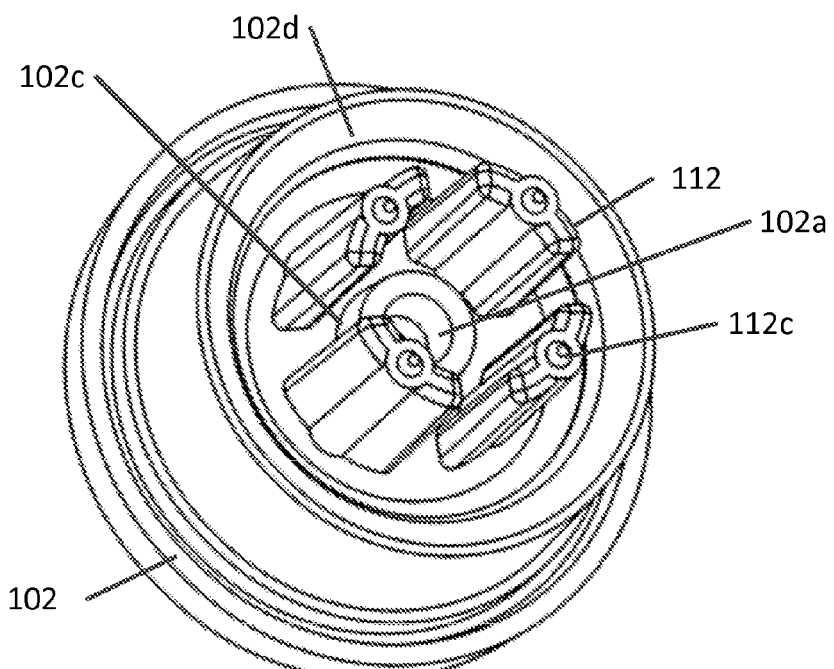
FIG. 6 is a perspective view of the lower housing of the embodiment of FIG. 1.

FIG. 5 shows a perspective view of upper housing 101 depicting fluid channel 115c, as shown, in fluid communication with first opening 101a and having a length generally parallel with the longitudinal axis of upper housing 101. The width of fluid channel 115c can be chosen to be approximately any width equal to a number greater than zero and less than of one half the maximum internal perimeter length of upper housing 101. In one aspect, fluid channel 115c width is chosen to be less than the minimum internal diameter of first opening 101a so as to facilitate a focused pressure or force (and/or accelerated fluid velocity) on peripheral wall 169 during infusion and/or flushing of device 100. FIG. 6 shows a perspective view of lower housing 102 depicting a plurality of supports 112 arranged about projection 102c of second opening 102a. Supports 112 are arranged radially around projection 102c with spacing therebetween so as to allow fluid communication between the upper housing 101 first opening 101a and lower housing 102 second opening 102a during infusion. Supports 112 can have distal projections 112c configured to contact lower surface of elastomeric member 110 and to minimize shifting of the elastomeric member 110 within the housing during assembly or use and/or to apply a preload and/or to account for the stack up of the upper and lower housing components.

FIGS. 7A and 7B are cross-sectional views of device 100 shown in a first state (e.g., infusion) and a second state (e.g., aspiration), respectively. Arrows A1 and A2 depict fluid flow direction within device 100.

With reference to FIG. 7A, in a first state, a pressure differential between the partitioned housing is created upon infusion of fluid through first opening 101a that causes deflection of peripheral wall 169 from interior wall 111 of upper housing 101 creating fluid passage 115 and allowing fluid communication between the upper portion and lower portion of device 100 around elastomeric member 110, while maintaining closure of slit 117, so as to provide directional fluid flow from first opening 101a through second opening 102a. Structures of lower housing 102, e.g., tapered wall 102d and projection 102c, can provide turbulence and/or fluid flow direction so as to enable effective flushing of elastomeric member portions that have been contacted with bodily fluids (e.g., the interior surface of peripheral wall 169). Peripheral wall 169, which in various aspects, provides an oval, cup-like, or conical frustum-shaped (or frustoconical), is configured to deflect and/or flex inward towards the central longitudinal axis of device 100 upon creating a differential in pressure, (for example through the introduction of infusion fluid the opening 101a) with a relatively low infusion cracking pressure threshold. A relatively low infusion cracking pressure threshold is that of approximately 6 to about 36 inches $H_2O$ (0.2 psig to about 1.3 psig; where the term "about" encompasses ±20% of the stated value). Such pressures are obtained, for example, when an IV bag is raised above the height of an insertion point in a patient. Unlike existing valves that flow "through" an elastomer seal/valve in both an infusion state and an aspiration state, the presently disclosed valve is configured to flow "around" the valve in an infusion state and through the valve in an aspiration state. The advantage of this present configuration is that leaking and "reflux" after aspiration is all but eliminated and the desirable ability to easily infuse fluid via gravity is provided as described with reference to the exemplary embodiment of FIGS. 7A and 73.

With reference to FIG. 7B, in a second state, a pressure differential created upon aspiration of fluid through the second opening 102a causes slit 117 to open whereas distal end 169a of peripheral wall 169 is maintained in continuous sealable interference contact with interior wall 111 of upper housing 101. In one aspect, the slit is configured such that an aspiration pressure threshold is required to allow fluid to pass through the slit from second opening 102a through first opening 101a. In one aspect, the aspiration pressure threshold is considerably higher than that of the infusion cracking pressure threshold. In one aspect the difference between the aspiration pressure threshold and that of the infusion aspiration threshold is such that the aspiration threshold cracking pressure is approximately 5 psig greater than that of the infusion threshold cracking pressure. This difference in threshold cracking pressure can range between about 3 psig and about 7 psig, (where "about" encompasses ±20% of the value). Configuring the difference in threshold cracking pressures can be accomplished by varying the elastic modulus, thickness and/or thickness variation, taper, cross-linking/cure, and material selection and dimensions of elastomeric member 110 as well as the design and arrangement of slit 117, discussed further below. Additional parameters that can be adjusted with regard to cracking pressure thresholds include the number, width, and length of flow channel 115c and/or internal geometries of upper and lower housing components.

Figure 8A:
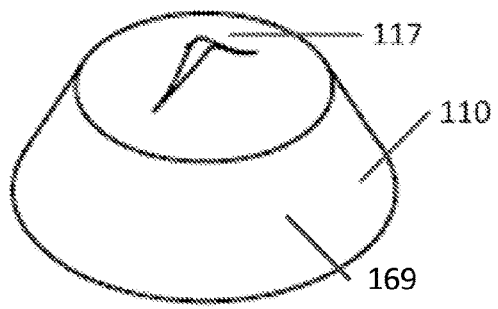
FIGS. 8A, 8B, 8C, and 8D are perspective views of the elastomeric member in accordance with embodiments of the present disclosure.
Figure 8B:
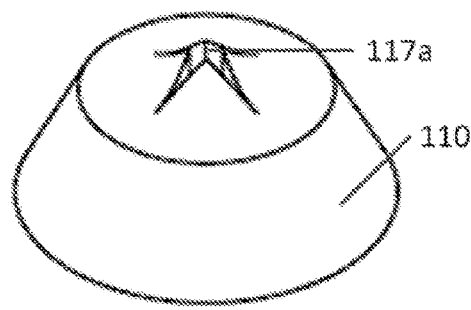

With reference to FIGS. 8A, 8B, 8C, and 8D, variations of the elastomeric member are shown. FIGS. 8A and 8B, depict elastomeric member 110 having a single slit 117 and multi-slit 117a configuration. Other slit configurations can be used.

Figure 8C:
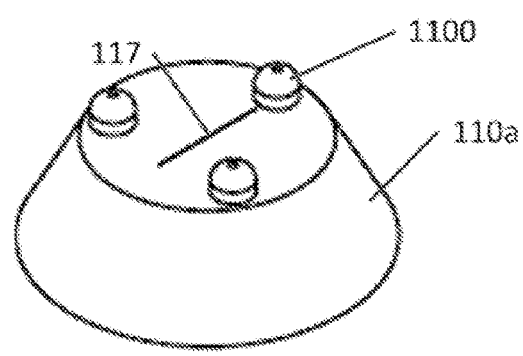
Figure 8D:
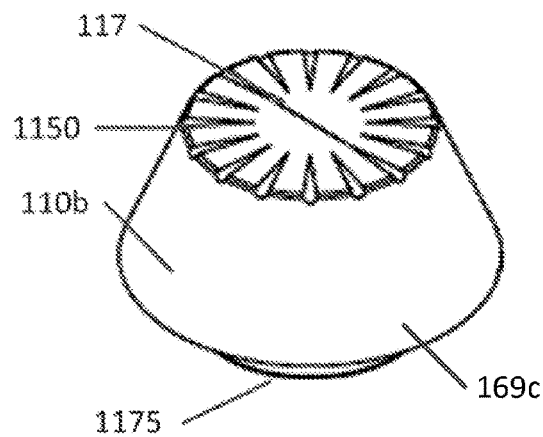

FIGS. 8C and 8D depict modified elastomeric members 110a and 110b, respectively, having additional features on the exemplary conical frustum-shaped member 110a, 110b, namely projections 1100 on surface of conical frustum-shaped member 110a, or one or more channels 1150 in the surface of conical frustum-shaped member 110b.

FIG. 8D further depicts an embodiment of the elastomeric member where in the conical frustum-shaped member 110b includes a stem 1175 with a conduit (not shown) there through surrounded by peripheral wall 169c, the conduit configured to surround second opening 102a or securely surround projection 102c of lower housing 101. Stem 1175 can be configured as a conduit for fluid communication with opening 102a and slit 117. In this configuration, stem 1175 necessarily comprises one or more vertically arranged (with housing longitudinal axis) openings/slits there through (not shown) for fluid passage/flushing during infusion, the opening/slits can be configured to respond to a compressive infusion pressure/force and at least partially open allowing fluid to enter opening 102a, whereas, during aspiration, the openings/slits, not subject to the compressive stress, would remain closed to facilitate substantially all fluid flow thru opening 102a, stem 1175, slit 117, upper section of housing and opening 101a. In this modification of the elastomeric member embodiment described above, all other functional attributes, as described above for elastomeric member 110, would be maintained.

With reference to FIG. 9, a second embodiment of the presently disclosed valve is shown, depicting a perspective view of device 200, having upper housing 201 with first opening 201a and lower housing 202.

FIG. 10 depicts a top view of device 200 with sectional planes 12A-12A and 12B-12B.

Figure 11A:
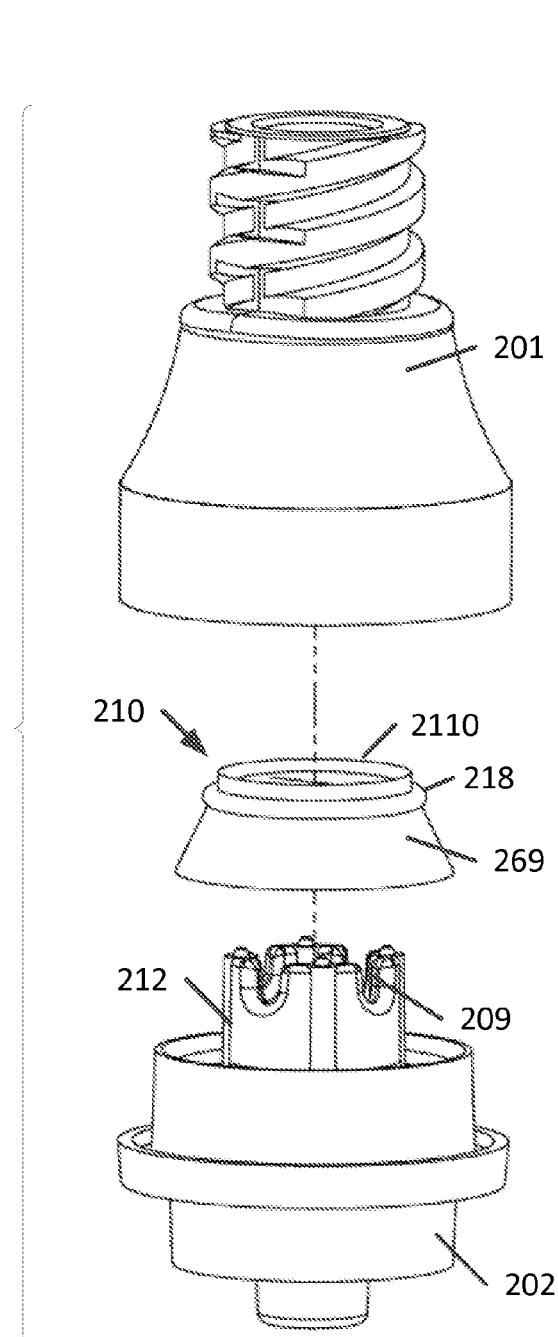
FIGS. 11A and 11B are an exploded view and exploded sectional view, respectively of the embodiment of FIG. 9.
Figure 11B:
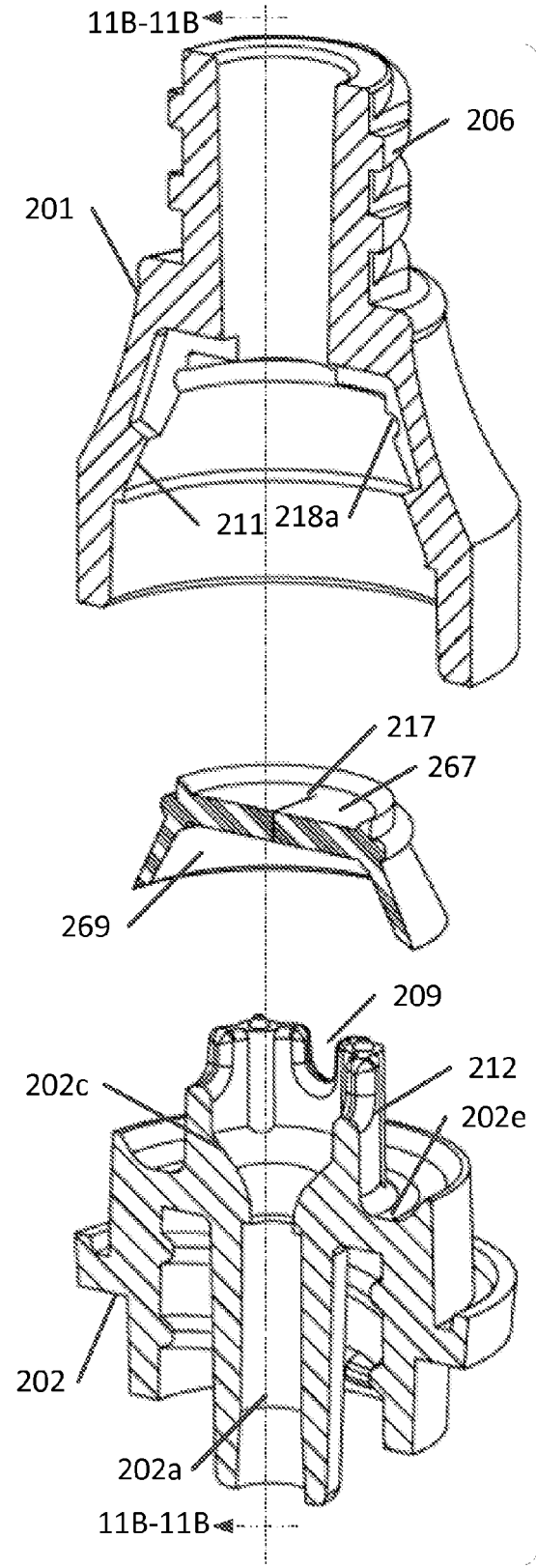

FIGS. 11A and 11B depict an exploded view an exploded sectional view, respectively of device 200. Lower housing 202 of device 200 includes annular wall 212. In this exemplary embodiment, annular wall 212 provides support to elastomeric member 210, which is surrounded by peripheral wall 269. Annular wall 212 can be integral with lower housing 201 as shown, or can be molded separately and arranged in housing during assembly. Elastomeric member 210 has lateral annular protrusion 218 from edge of surface 267 configured to be received by recess 218a within interior wall 211 of upper housing 201. In addition, elastomeric member 210 includes vertical annular projection 2110 from surface 267 for providing interference upon assembly of upper and lower housing components 201, 202. Surface 267 of elastomeric member 210 includes slit 217, which passes through the thickness of surface 267. Differing from the previous embodiment, lower housing 202 of device 200 includes tapered opening 202c feeding into second opening 202a. Tapered opening 202c provides guidance for insertion of medical devices such as guide wires, etc. into smaller diameter second opening 201a and prevents kinking and/or bending of such devices.

Figure 12A:
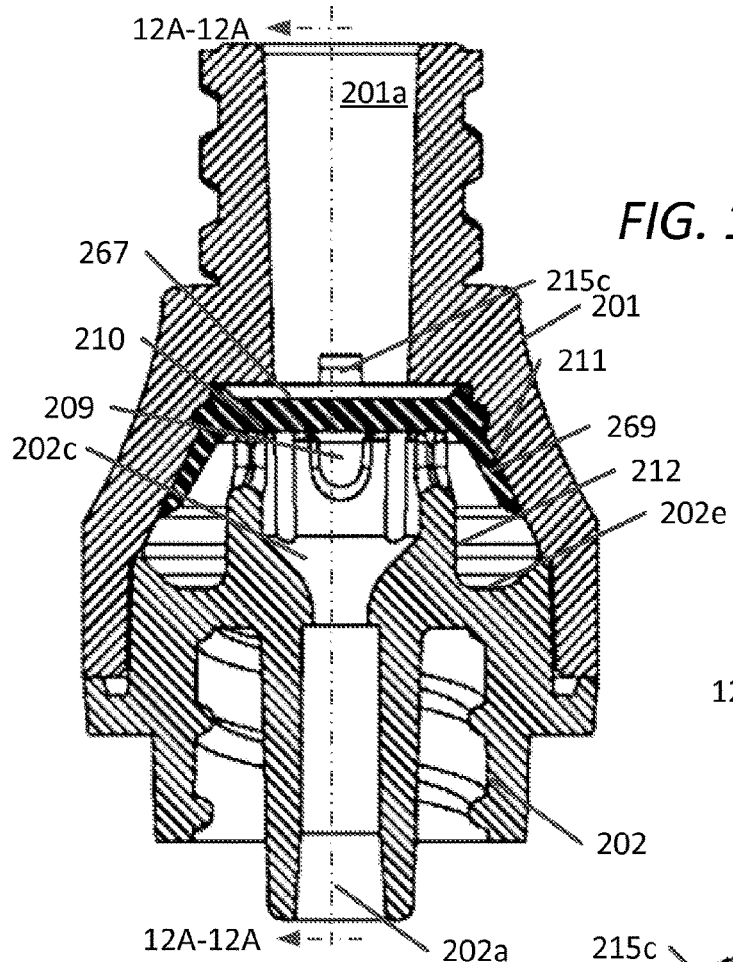
FIG. 12A and FIG. 12B are cross-sectional views of the embodiment of FIG. 9 along sectional planes 12A-2A and 12B-12B, respectively.
Figure 12B:
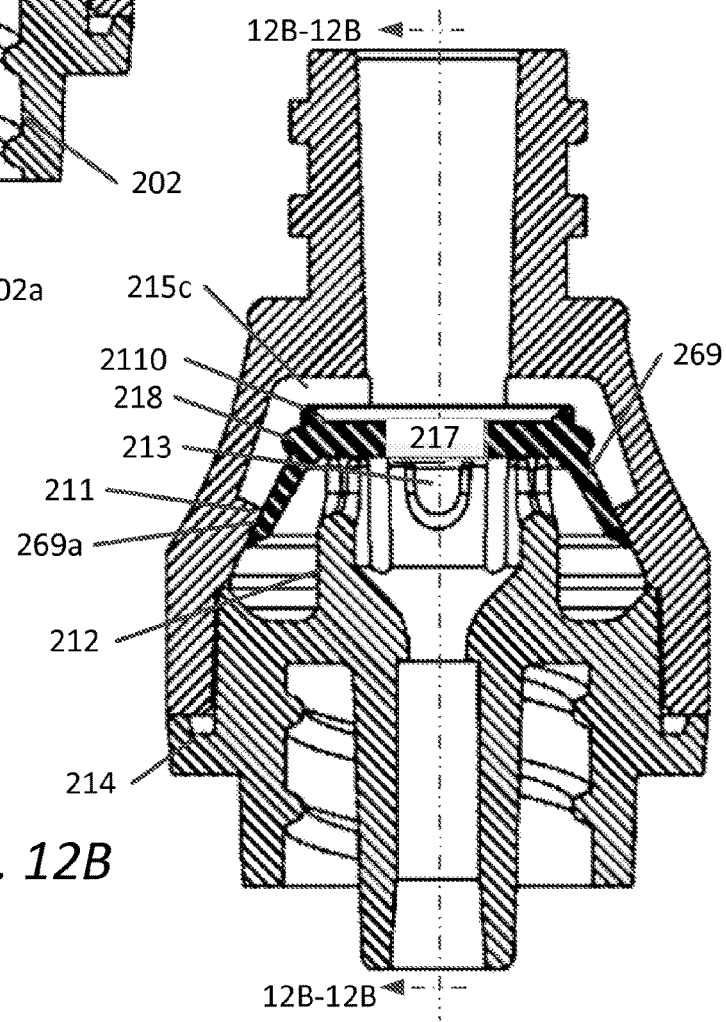

Referring now to FIGS. 12A and 12B, cross-sectional views, 90° apart, respectively, of second embodiment device 200 in an assembled configuration are shown. FIG. 12A depicts a portion of peripheral wall 269 of elastomeric member 210 having an interference fit with the interior wall 211 forming a continuous seal with the interior wall 211 of upper housing 201. Elastomeric member 210 partitions device 200 into an upper section corresponding to first opening 201a and lower section corresponding to second opening 202a. Elastomeric member 210 is shown supported by annular projection 212 that includes flow passages 209 that provide fluid communication between lower housing 202 and through second opening 202a. Elastomeric member 210 is shown here as a normally-closed valve, as both slit 217 and continuous seal with interior wall 211 prevent fluid flow between openings 201a and 202a prior to activation of device 200 via a pressure differential. The interference fit between elastomeric member 210 and interior housing wall 211 can be provided upon securing upper housing 201 and lower housing 202 during manufacturing e.g., upon bonding/welding the housings components together, for example at weld joint 214. The peripheral wall 269 of elastomeric member 210 forms a fluid-type seal with interior wall 211. Fluid is able to flow through annular support 212 at openings 209 and second opening 202a. Lower housing 202 includes surface or base 202e surrounding annular support 212 which projects from base 202e as part of second opening 202a. Surface or base 202e extends radially outward to tapered wall 202d. A portion of the outer diameter of tapered wall 202d is configured for sealable arrangement via weld joint 214 with an interior diameter of upper housing 201. FIG. 12B depicts an aspect of the second embodiment whereby interior diameter of annular support 212 tapers inwardly to that of internal diameter of second opening 202a which also serves as guiding means for medical devices that may be inserted through the device.

In a manner similar to that of the first embodiment, device 200 comprises optional fluid channel 215c that extends generally parallel to the longitudinal axis of device 200 towards lower housing 202. In one embodiment, any of the devices herein disclosed can be configured without fluid channel 215c.

Figure 13A:
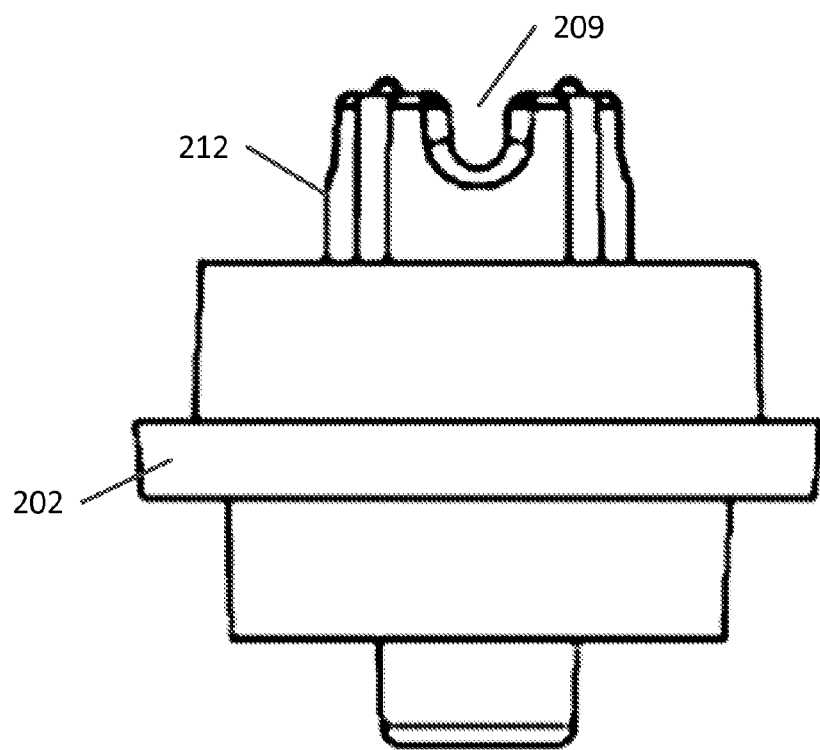
FIGS. 13A and 13B are a plan view and a perspective view of the lower housing, respectively, of the embodiment of FIG. 9.
Figure 13B:
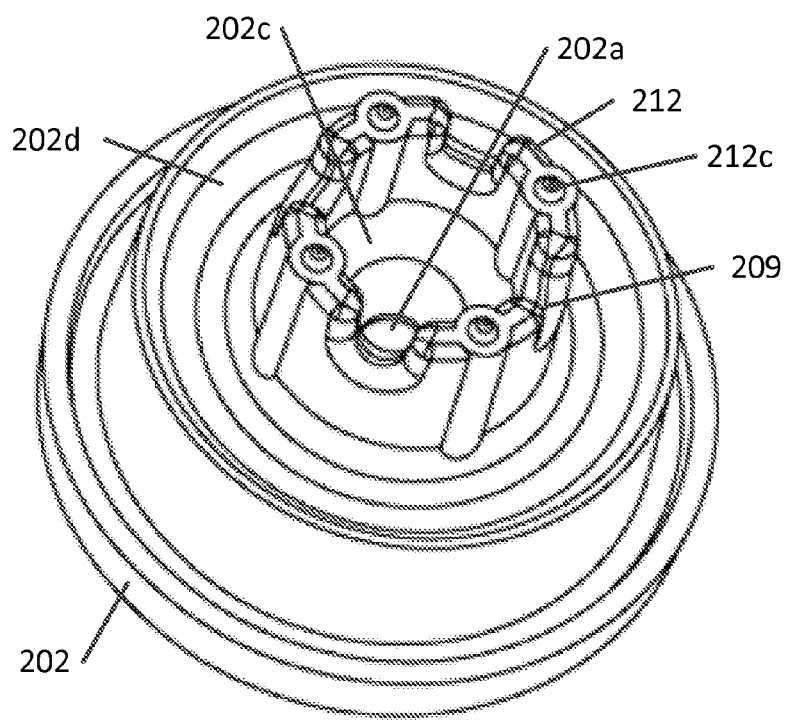

FIG. 13A shows a side view of lower housing 202 depicting annular support 212 and passage 209. FIG. 13B is a perspective view of lower housing 202 showing annular support 212 and tapered opening 202f feeding into second opening 202a. Annular support 212 can have distal projections 212c configured to contact lower surface of elastomeric member 210 and to minimize shifting of the elastomeric member 210 within the housing during assembly or use.

Device 200 functions similarly as that of the first embodiment, as depicted in FIGS. 14A and 14B, which show cross-sectional views of device 200 shown in a first state (e.g., infusion) and a second state (e.g., aspiration), respectively. Arrows B1 and B2 depict fluid flow direction within device 200. With reference to FIG. 14A, in a first state, a pressure differential is created between the partitioned housing of device 200 upon infusion of fluid through first opening 201a that causes deflection of peripheral wall 269 from interior wall 211 of upper housing 201 creating fluid passage 215 and allowing fluid communication between the upper portion and lower portion of device 200 around elastomeric member 210, while maintaining closure of slit 217, so as to provide directional fluid flow from first opening 201a through second opening 202a. Structures of lower housing 202, e.g., tapered wall 202d can provide turbulence and/or fluid flow direction so as to enable effective flushing of elastomeric member portions that have been contacted with bodily fluids (e.g., the interior surface of peripheral wall 269). Peripheral wall 269 is configured to deflect and/or flex inward towards the central longitudinal axis of device 200 upon creating a differential in pressure, (for example through the introduction of infusion fluid the opening 201a) with a relatively low infusion cracking pressure threshold as previously described for the first embodiment.

With reference to FIG. 14B, in a second state, a pressure differential in the partitioned housing is created upon aspiration of fluid through the second opening 202a that causes slit 217 to open whereas distal edge 269a of peripheral wall 269 is maintained in continuous sealable interference contact with interior wall 211 of upper housing 201. In one aspect, the slit is configured such that an aspiration pressure threshold is required to allow fluid to pass through the slit from second opening 202a through first opening 201a.

FIGS. 15A and 15B depict a third embodiment device 300 shown configured with upper housing 201 and elastomeric member 210 from the second embodiment device 200, whereas annular support 312 having opening 309 is configured so as not to contact the lower surface of elastomeric member 210. Support of elastomeric member 210 is provided solely by lateral annular protrusion 218 and interference with recess 218a as discussed above. FIG. 15C depicts device 333, which has a modification to the lower housing component of device 300, where annular support 312 is completely absent, and surface or base 302e of lower housing 302' has opening 302c to feed into second opening 302a.

Figures 16A, 16B:
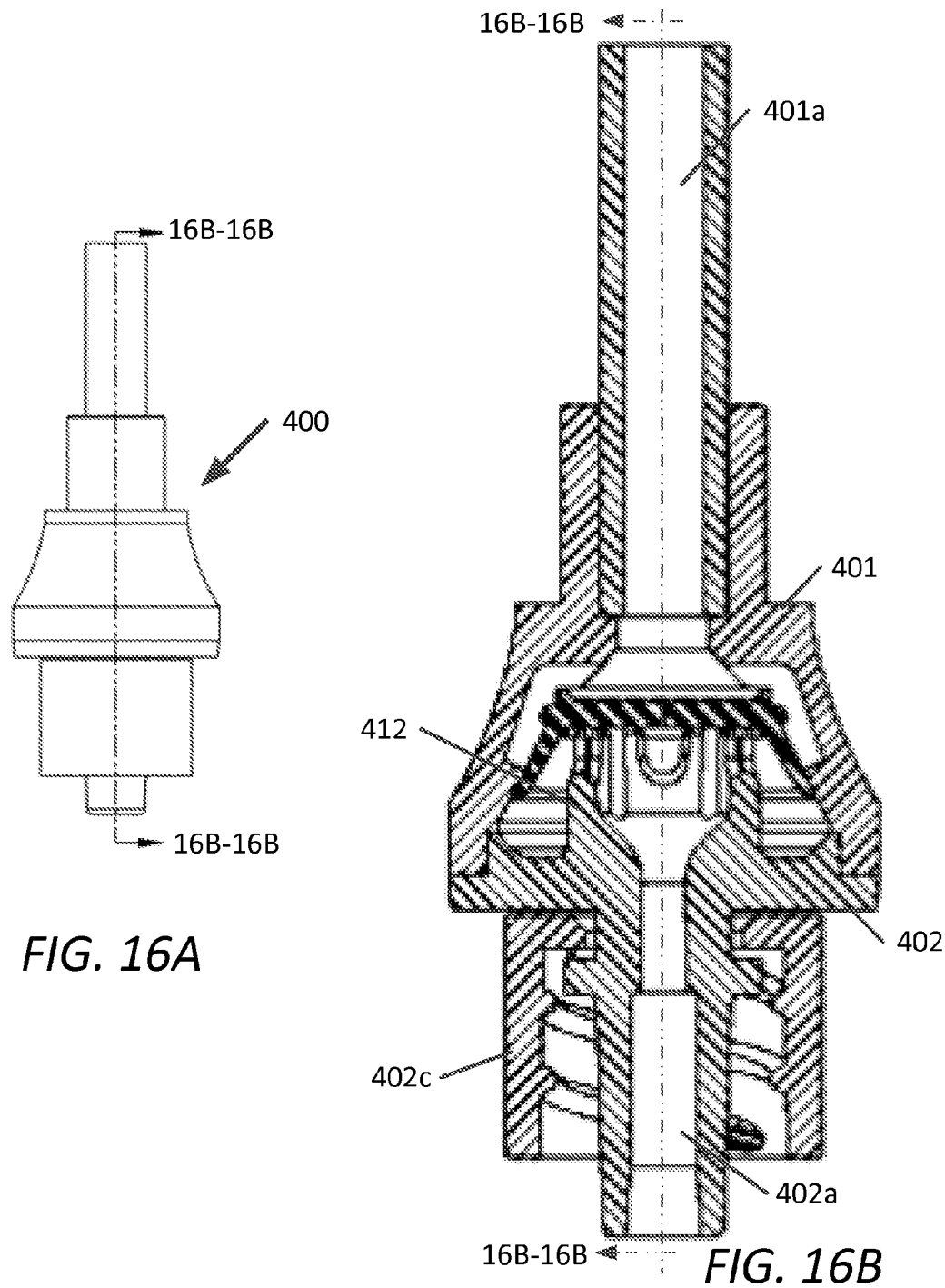
FIG. 16A is a plan view, with sectional plane 16B-16B, of another embodiment of a pressure activated valve in accordance with the present disclosure.
FIG. 16B is a cross-sectional view along sectional plane 16B-16B, of the embodiment of FIG. 16A.

FIGS. 16A and 16B are a perspective view and cross-sectional view along sectional plane 16B-16B of a fourth embodiment device 400 showing implementation of the pressure activated valve with a male luer lock housing assembly. Tubing 401a is bonded to tube housing 401, which is joined to male luer housing 402. Male luer lock hub 402c is snap fit to lower housing 402. The function and operation of device 400 is that as similarly described for the previously described embodiments.

Figures 17A, 17B:
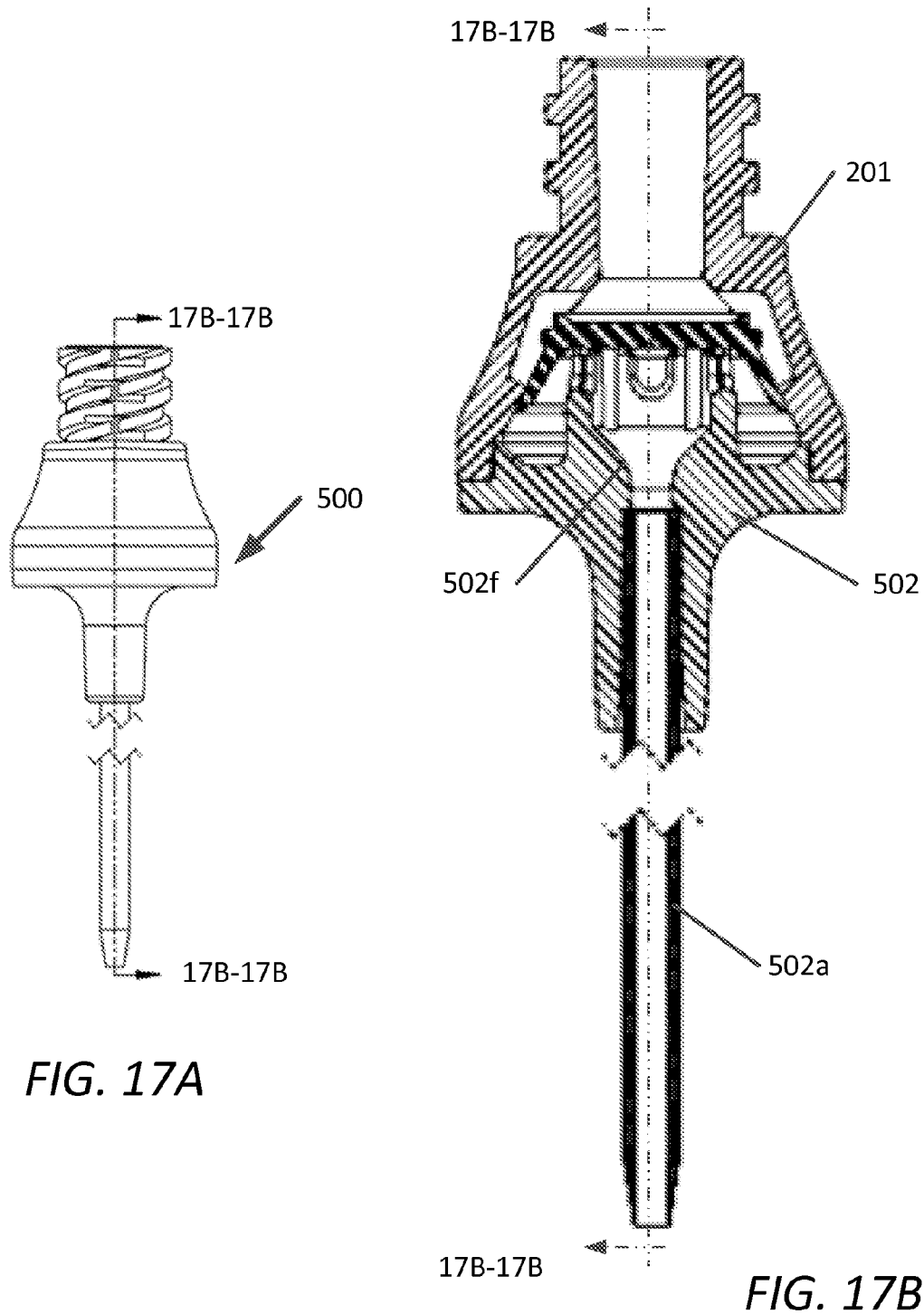
FIG. 17A is a plan view, with sectional plane 17B-17B, of another embodiment of a pressure activated valve in accordance with the present disclosure.
FIG. 17B is a cross-sectional view along sectional plane 17B-17B, of the embodiment of FIG. 17A.

FIGS. 17A and 17B are a perspective view and cross-sectional view along sectional plane 17B-17B, respectively, of a fifth embodiment, device 500 assembled with upper housing 201. Device 500 demonstrates how pressure activated valve can be integrated directly into a vascular catheter hub 502. Catheter 502a can be a peripheral IV catheter, a PICC, a CVC, or the like.

Figures 18A, 18B:
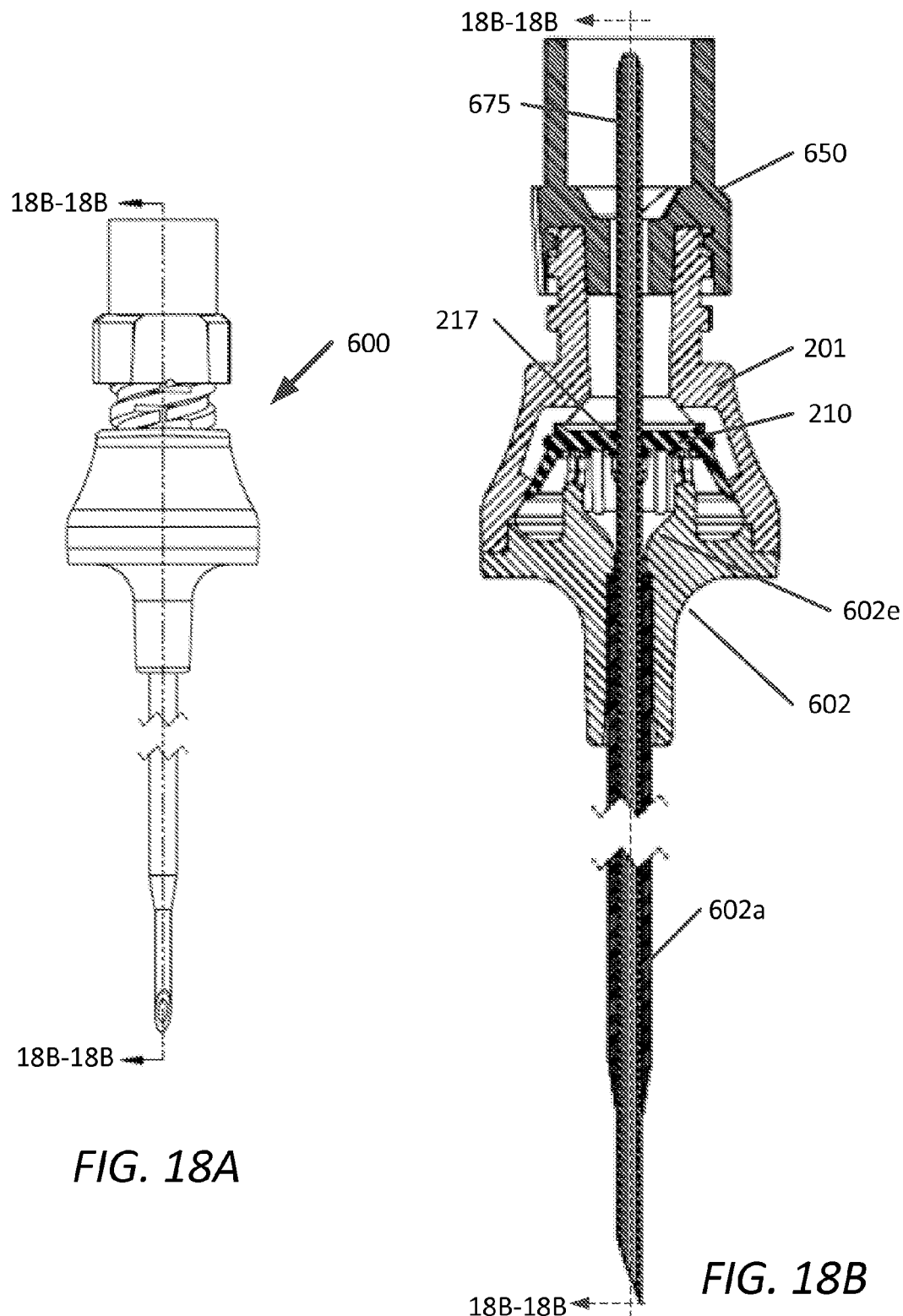
FIG. 18A is a plan view, with sectional plane 18B-18B, of another embodiment of a pressure activated valve in accordance with the present disclosure.
FIG. 18B is a cross-sectional view along sectional plane 18B-18B, of the embodiment of FIG. 18A.

FIGS. 18A and 18B are a perspective view and cross-sectional view along sectional plane 18B-18B, respectively, of a fifth embodiment, device 600 assembled with upper housing 201 and further coupled with male Luer device 650. Device 600 demonstrates how slit 217 of elastomeric member 210 can accommodate medical device 675 inserted through catheter 602a, guided by tapered internal conduit 602e.

Figures 19A, 19B:
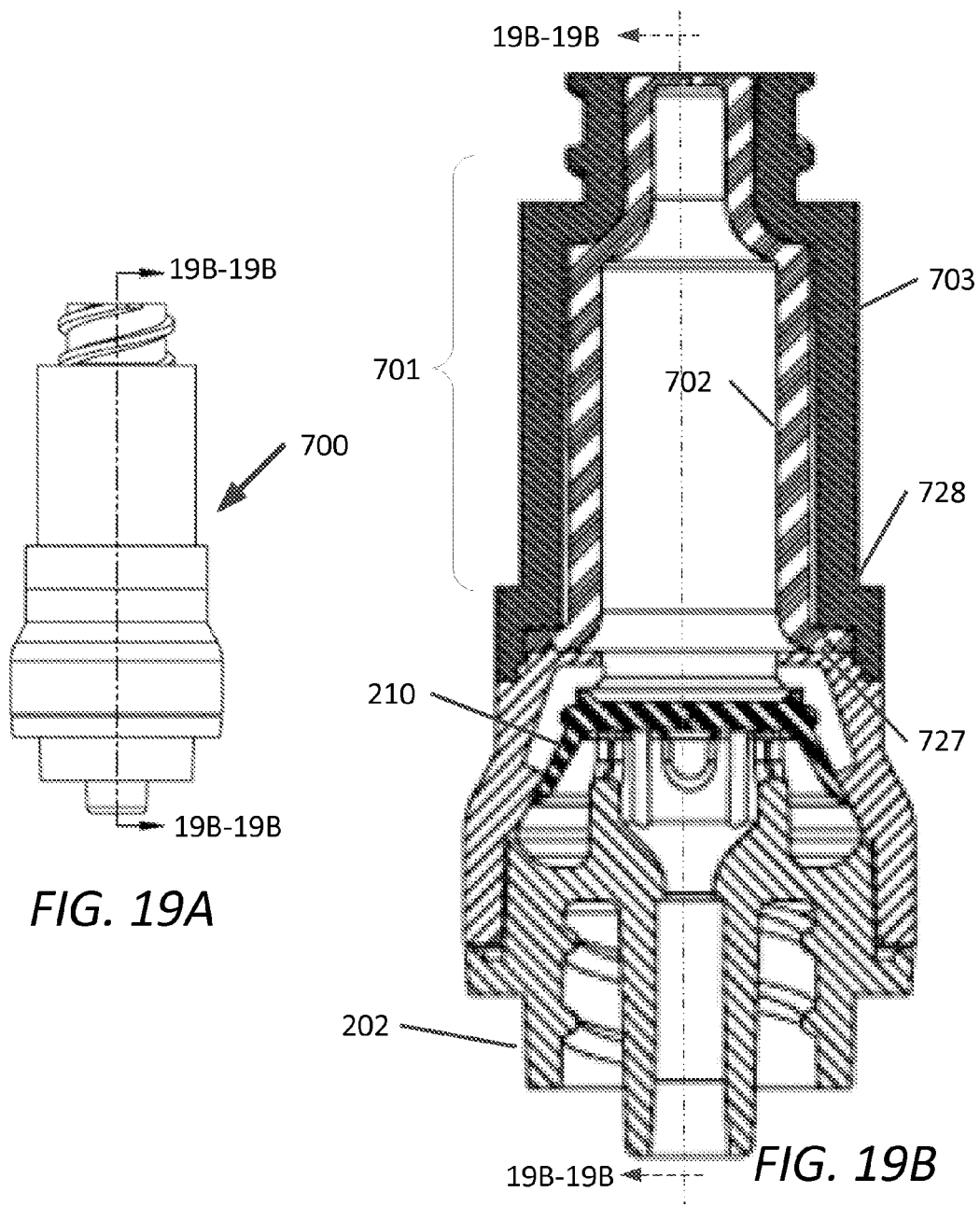
FIG. 19A is a plan view, with sectional plane 19B-19B, of another embodiment of a pressure activated valve in accordance with the present disclosure.
FIG. 19B is a cross-sectional view along sectional plane 19B-19B, of the embodiment of FIG. 19A.

FIGS. 19A and 19B are a perspective view and cross-sectional view along sectional plane 19B-19B, respectively, of a sixth embodiment, device 700. Device 700 demonstrates the pressure activated valve of the present disclosure integrated directly with luer-activated valve 701. The pressure activated valve assembly is joined to the luer activated valve assembly at 727. Luer activated valve 701 is assembled into female luer housing 703 and is sealed within it at 728. Device 700 comprising Luer activated valve as shown is an example of one valve, however the pressure activated valve assembly can be integrated with any number of luer activated valves to provide for the benefits as disclosed herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated' listed items.

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise.

It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof Unless otherwise defined, all terms (including technical and scientific terms) used herein have the same meaning as commonly understood by one of ordinary skill in the art to which this present disclosure belongs. It will be further understood that terms used herein should be interpreted as having a meaning that is consistent with their meaning in the context of this specification and the relevant art and will not be interpreted in an idealized or overly formal sense unless expressly so defined herein.

Unless otherwise expressly stated, comparative, quantitative terms such as "less" and "greater", are intended to encompass the concept of equality. As an example, "less" can mean not only "less" in the strictest mathematical sense, but also, "less than or equal to."

The term "fluid" as used herein refers to a liquid, gas, or combination thereof.

We claim:

1. A valve comprising:
a housing having an interior wall, a first opening and a second opening, wherein the housing comprises two or more components sealably connectable to form a fluid tight assembly; and
an elastomeric member positioned in the housing, the elastomeric member comprising:
a continuous peripheral wall projecting from a surface; and
a slit extending through the surface, a continuous portion of the peripheral wall creating a continuous sealable contact with the interior wall of the housing and partitioning the housing into an upper section and a lower section, the elastomeric member configured such that upon creating a pressure differential between the upper section and the lower section of the housing:
(i) upon infusion of a fluid through the first opening, the peripheral wall is deflected from the interior wall of the housing to create a fluid passage around the elastomeric member; and
(ii) upon aspiration of a fluid through the second opening, the slit opens whereas, a distal end of peripheral wall maintains a continuous sealable interference contact with the interior wall, permitting fluid flow through the elastomeric member;
wherein an upper portion of the housing comprises the interior wall, the interior wall comprising at least one recessed channel therein and extending substantially along the longitudinal axis of the housing, wherein deflection of the peripheral wall from the housing substantially corresponds to the placement of the at least one recessed channel.

2. The valve of claim 1, further comprising a support member positioned in the housing and surrounded by the peripheral wall, the support member configured to provide fluid communication between the first opening and the second opening.

3. The valve of claim 2, wherein the support member comprises a plurality of spaced apart columns arranged about the second opening, the distal ends of the plurality of columns surrounded by the peripheral wall.

4. The valve of claim 2, wherein the support member comprises an annular wall arranged around the second opening, the annular wall having at least one fluid flow passage providing fluid communication between the lower section and the second opening.

5. The valve of claim 2, wherein the second opening comprises a conduit that extends into the housing and is surrounded the peripheral wall, wherein a first portion of the conduit extending into the housing is of a larger internal diameter than a second portion of the conduit extending external to the housing.

6. The valve of claim 2, wherein the support member is configured to receive and/or guide an elongated medical device through the housing.

7. The valve of claim 2, wherein the support member in combination with the slit is configured to receive and/or guide an elongated medical device through the housing.

8. The valve of claim 1, wherein a portion of the housing is tapered and a distal portion of the peripheral wall tapers in sealable contact therewith.

9. The valve of claim 1, wherein the surface comprises a top surface and a bottom surface separated from the top surface by a first thickness; and the peripheral wall has a second thickness, and the peripheral wall projects from the bottom surface.

10. The valve of claim 9, wherein the second thickness is less than the first thickness.

11. The valve of claim 9, wherein the elastomeric member further comprises one or more vertical protrusions on the top surface, the housing being configured to provide a normal stress to the one or more vertical protrusions.

12. The valve of claim 9, wherein the thickness is concave, convex, or concave and convex on opposing sides of the thickness.

13. The valve of claim 9, wherein the top surface of the elastomeric member has one or more fluid channels terminating at a peripheral edge.

14. The valve of claim 1, wherein the elastomeric member further comprises a continuous lateral protrusion along a peripheral edge of the surface, and the housing is configured with a corresponding recess to receive the continuous lateral protrusion and to provide a radial stress to the surface of the elastomeric member.

15. The valve of claim 1, wherein the elastomeric member is annular, oval, cylindrical, hemispherical, or cup-shaped.

16. The valve of claim 1, wherein the elastomeric member is conical frustum-shaped.

17. The valve of claim 1, wherein the slit opens at a threshold pressure greater than a threshold pressure required to deflect the peripheral wall from the housing.

18. The valve of claim 1, wherein the slit, in combination with the first opening and the second opening, is configured to receive an elongated medical device through the housing.

19. A method of controlling flow direction through a device, the method comprising:
   creating, in a device comprising the valve as defined in claim 1, a pressure differential between the upper section and the lower section of the housing;
   causing the peripheral wall to deflect from the housing and permitting fluid flow around the elastomeric member; or
   causing the slit to open permitting fluid aspiration through the elastomeric member;
wherein fluid flow direction through the device is controlled.

20. The method of claim 19, wherein the pressure differential between the upper section and the lower section of the housing is created by a negative pressure applied to the upper section of the housing or by a positive pressure applied to the lower section of the housing so that the slit permits fluid flow therethrough.

21. The method of claim 19, wherein the pressure differential between the upper section and the lower section of the housing is created by a positive pressure applied to the upper section of the housing so that the peripheral wall permits fluid flow around the elastomeric member.

22. The method of claim 19, further comprising:
   introducing a flushing solution to the upper section of the housing via the first opening;
   causing, by positive pressure, deflection of the peripheral wall from the housing;
   urging the flushing solution around the elastomeric member;
   re-directing fluid flow in the lower section of the housing; and
   cleaning at least a portion of the lower section of the housing.

23. The method of claim 22, wherein the cleaning prevents thrombus or bacterial growth within the device after aspiration of biological fluid through the device.

24. The method of claim 19, wherein reflux is prevented within the device.

25. A device comprising a valve as defined in claim 1.

* * * * *